United States Patent
Scheller et al.

(10) Patent No.: US 9,480,602 B2
(45) Date of Patent: *Nov. 1, 2016

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/678,740

(22) Filed: Apr. 3, 2015

(65) Prior Publication Data

US 2015/0209182 A1 Jul. 30, 2015

Related U.S. Application Data

(63) Continuation of application No. 13/893,701, filed on May 14, 2013, now Pat. No. 9,023,020.

(51) Int. Cl.
*A61F 9/008* (2006.01)
*A61B 18/00* (2006.01)
*A61B 18/22* (2006.01)

(52) U.S. Cl.
CPC .. *A61F 9/00823* (2013.01); *A61B 2018/00589* (2013.01); *A61B 2018/2238* (2013.01); *A61F 2009/00863* (2013.01)

(58) Field of Classification Search
CPC ........... A61B 17/2909; A61B 2017/00367; A61B 2017/2913; A61B 2017/2918; A61B 2017/00424; A61B 2017/0042
See application file for complete search history.

(56) References Cited

U.S. PATENT DOCUMENTS

| | | |
|---|---|---|
| 5,190,050 A | 3/1993 | Nitzsche |
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 6,123,699 A | 9/2000 | Webster, Jr. |
| 6,126,654 A | 10/2000 | Giba et al. |
| 6,198,974 B1 | 3/2001 | Webster, Jr. |

(Continued)

FOREIGN PATENT DOCUMENTS

| | | |
|---|---|---|
| EP | 0900547 B1 | 3/1999 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Gary Jackson
*Assistant Examiner* — Scott T Luan
(74) *Attorney, Agent, or Firm* — Kevin P. Rollins

(57) ABSTRACT

A steerable laser probe may include a handle having a handle distal end and a handle proximal end, an actuation structure of the handle, a flexible housing tube having a flexible housing tube distal end and a flexible housing tube proximal end, and an optic fiber disposed within an inner bore of the handle and the flexible housing tube. A compression of the actuation structure may cause the optic fiber to gradually curve. A decompression of the actuation structure may cause the optic fiber to gradually straighten.

20 Claims, 24 Drawing Sheets

(56) References Cited

U.S. PATENT DOCUMENTS

| | | |
|---|---|---|
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | Mc Gowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0272975 A1 | 12/2005 | McWeeney et al. |
| 2005/0277874 A1 | 12/2005 | Selkee |
| 2007/0185514 A1 | 8/2007 | Kirchhevel |
| 2009/0018393 A1 | 1/2009 | Dick et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0268234 A1 | 10/2010 | Aho et al. |
| 2011/0028947 A1 | 2/2011 | Scheller et al. |
| 2012/0116361 A1* | 5/2012 | Hanlon et al. .......... 606/1 |
| 2013/0035551 A1* | 2/2013 | Yu et al. ............. 600/141 |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |

* cited by examiner

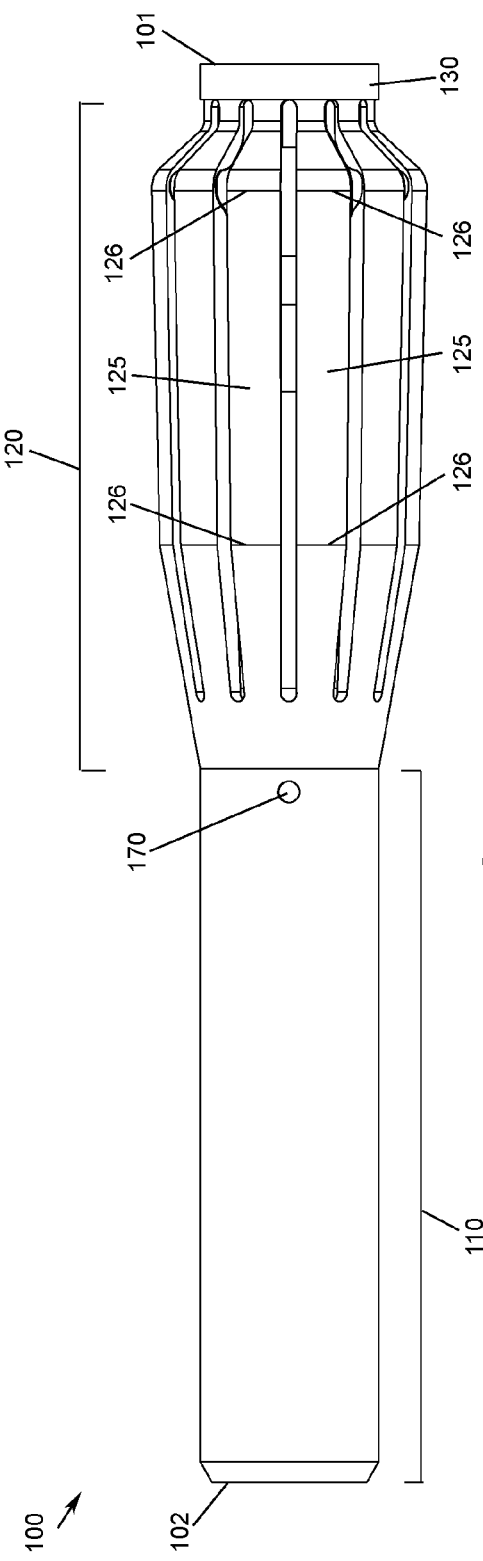
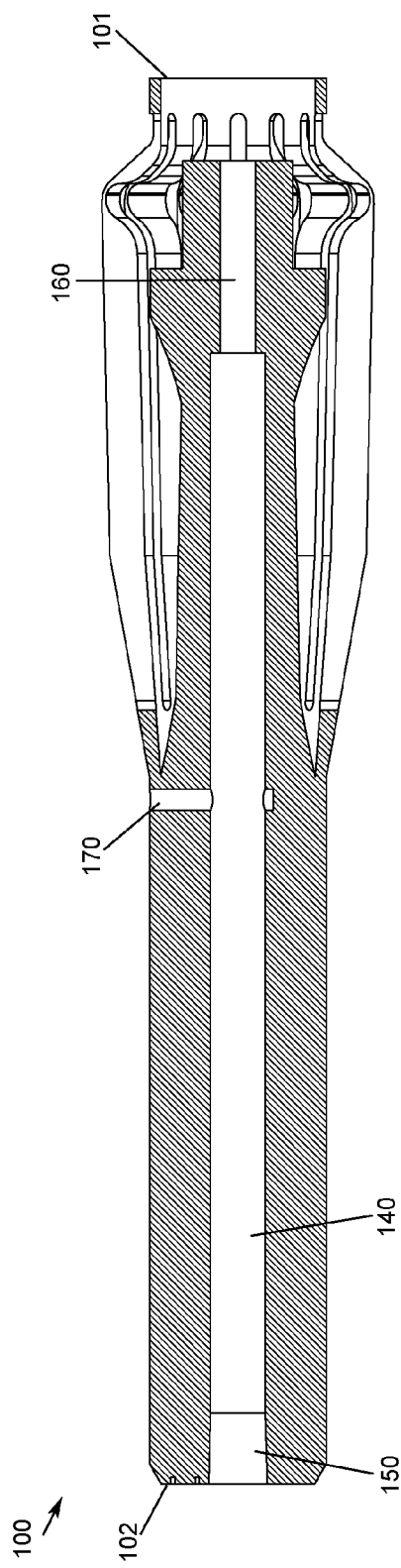
FIG. 1A
FIG. 1B

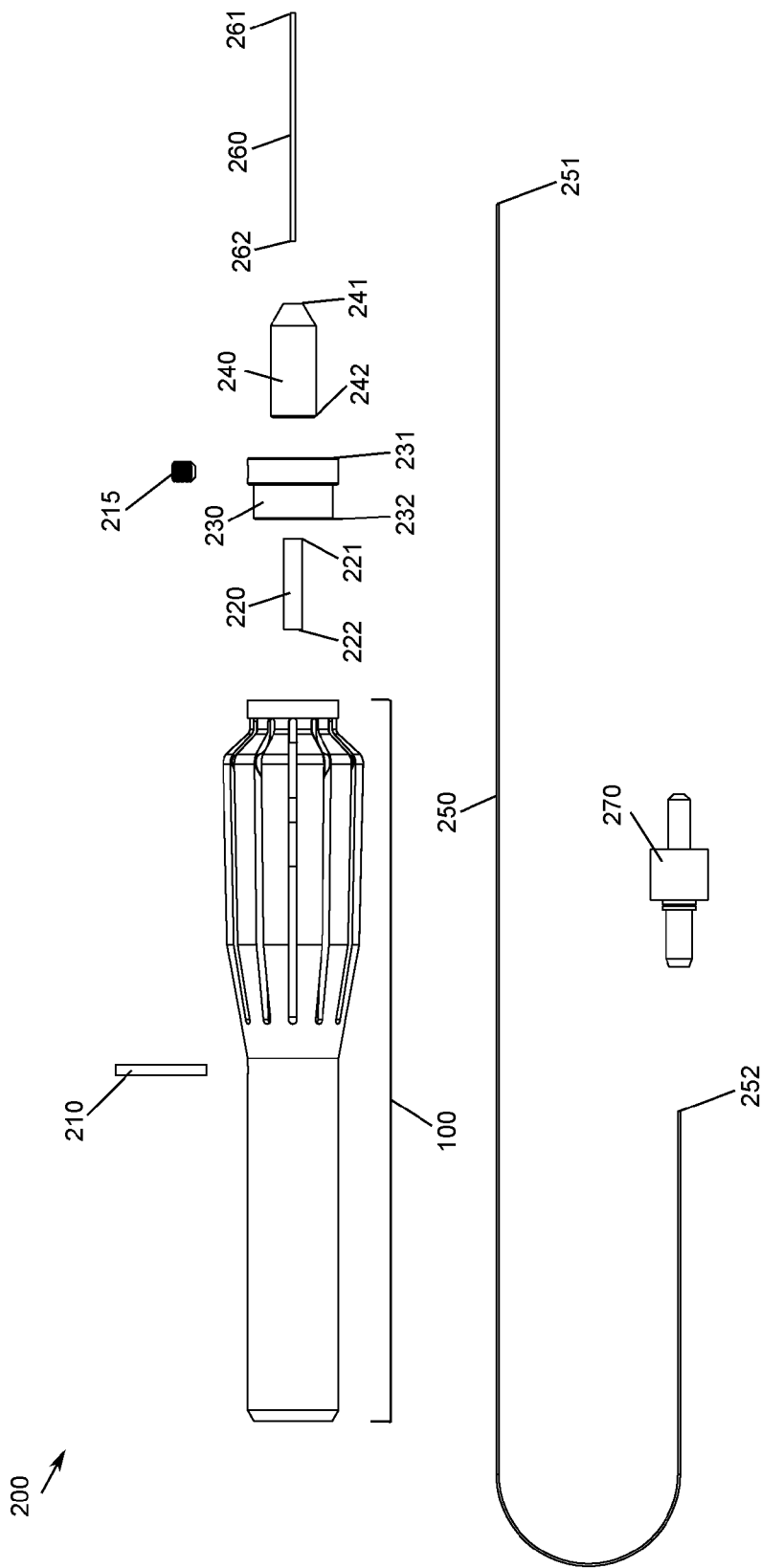

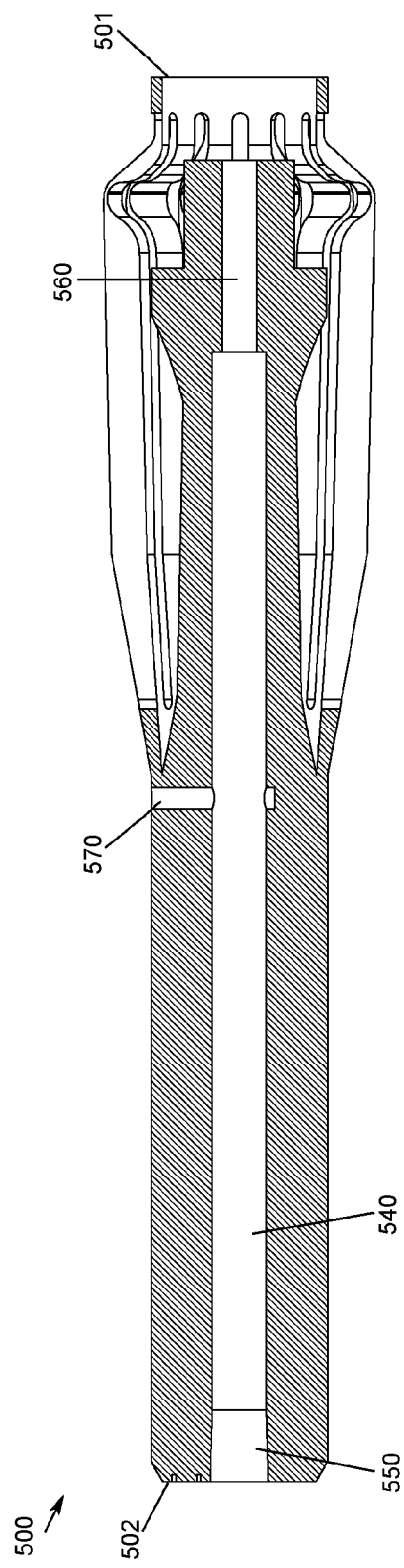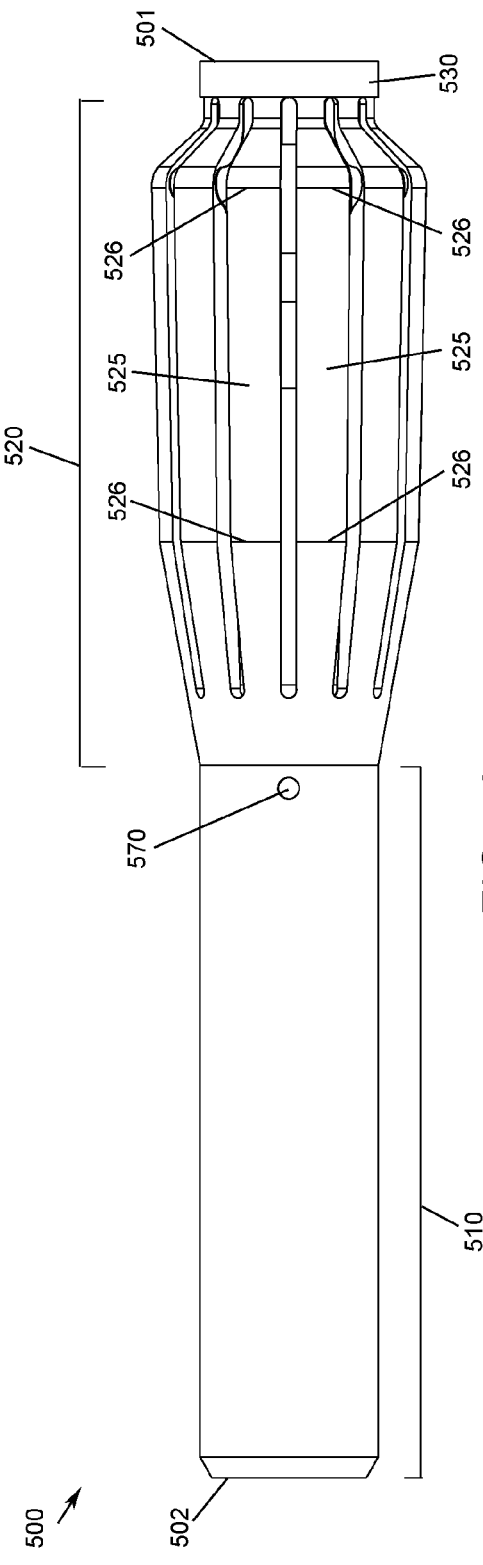
FIG. 5B
FIG. 5A

US 9,480,602 B2

STEERABLE LASER PROBE

CROSS-REFERENCE TO RELATED APPLICATIONS

This application is a continuation of prior application Ser. No. 13/893,701, filed May 14, 2013.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle having a handle distal end and a handle proximal end, an actuation structure of the handle, a flexible housing tube having a flexible housing tube distal end and a flexible housing tube proximal end, and an optic fiber disposed within an inner bore of the handle and the flexible housing tube. Illustratively, a compression of the actuation structure may be configured to gradually curve the flexible housing tube. In one or more embodiments, a gradual curving of the flexible housing tube may be configured to gradually curve the optic fiber. Illustratively, a decompression of the actuation structure may be configured to gradually straighten the flexible housing tube. In one or more embodiments, a gradual straightening of the flexible housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIG. 2 is a schematic diagram illustrating an exploded view of a steerable laser probe assembly;

FIGS. 5A and 5B are schematic diagrams illustrating a handle;

DETAILED DESCRIPTION OF AN ILLUSTRATIVE EMBODIMENT

Figure 3A:
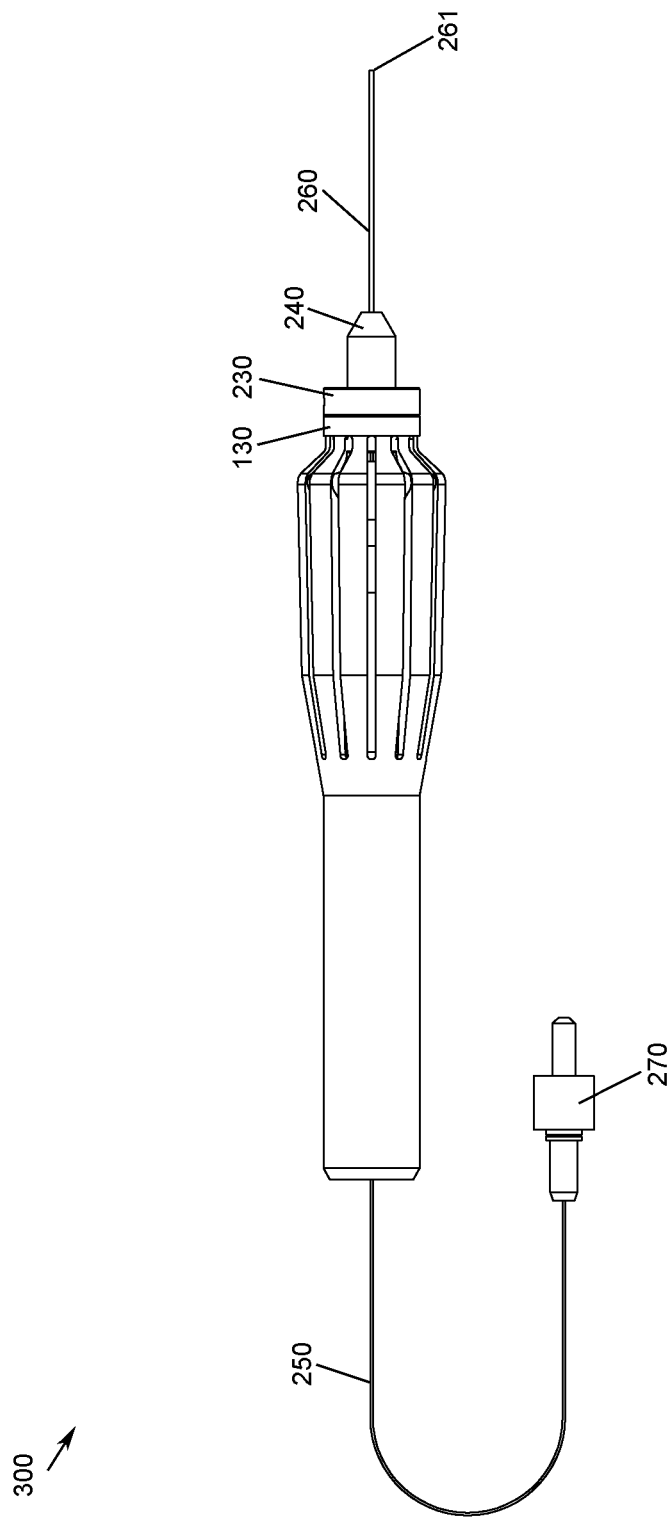
FIGS. 3A, 3B, 3C, 3D, and 3E illustrate a gradual curving of an optic fiber.

FIGS. 1A and 1B are schematic diagrams illustrating a handle 100. FIG. 1A illustrates a top view of handle 100. In one or more embodiments, handle 100 may comprise a handle distal end 101, a handle proximal end 102, a handle base 110, and an actuation structure 120. Illustratively, actuation structure 120 may comprise an actuation structure distal end 121 and an actuation structure proximal end 122. In one or more embodiments, actuation structure 120 may comprise a plurality of actuation arms 125. Illustratively, each actuation arm 125 may comprise at least one extension mechanism 126. In one or more embodiments, actuation structure 120 may comprise a shape memory material configured to project actuation structure distal end 121 a first distance from actuation structure proximal end 122, e.g., when actuation structure 120 is fully decompressed. Illustratively, actuation structure 120 may comprise a shape memory material configured to project actuation structure distal end 121 a second distance from actuation structure proximal end 122, e.g., when actuation structure 120 is fully compressed. In one or more embodiments, the second distance from actuation structure proximal end 122 may be greater than the first distance from actuation structure proximal end 122. Actuation structure 120 may be manufactured from any suitable material, e.g., polymers, metals, metal alloys, etc., or from any combination of suitable materials.

Illustratively, actuation structure 120 may be compressed by an application of a compressive force to actuation structure 120. In one or more embodiments, actuation structure 120 may be compressed by an application of one or more compressive forces located at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 from any rotational position of a plurality of rotational positions of handle 100.

In one or more embodiments, actuation structure 120 may be compressed by an application of a compressive force to any one or more of the plurality of actuation arms 125. Illustratively, each actuation arm 125 may be configured to actuate independently. In one or more embodiments, each actuation arm 125 may be connected to one or more of the plurality of actuation arms 125 wherein an actuation of a particular actuation arm 125 may be configured to actuate every actuation arm 125 of the plurality of actuation arms 125. Illustratively, one or more actuation arms 125 may be configured to actuate in pairs or groups. For example, an actuation of a first actuation arm 125 may be configured to actuate a second actuation arm 125.

In one or more embodiments, a compression of actuation structure 120, e.g., due to an application of a compressive force to a particular actuation arm 125, may be configured to actuate the particular actuation arm 125. Illustratively, an actuation of the particular actuation arm 125 may be configured to actuate every actuation arm 125 of the plurality of actuation arms 125. In one or more embodiments, an application of a compressive force to a particular actuation arm 125 may be configured to extend at least one extension mechanism 126 of the particular actuation arm 125. Illustratively, a particular actuation arm 125 may be configured to extend a first length from handle base 110. An extension of an extension mechanism 126 of the particular actuation arm 125, e.g., due to an application of a compressive force to the particular actuation arm 125, may be configured to extend the particular actuation arm 125 a second length from handle base 110. Illustratively, the second length from handle base 110 may be greater than the first length from handle base 110.

In one or more embodiments, handle 100 may comprise an actuation ring 130 fixed to actuation structure distal end 121. Illustratively, a compression of actuation structure 120 may be configured to gradually extend actuation ring 130 from handle base 110. For example, actuation ring 130 may be configured to extend a first distance from actuation structure proximal end 122, e.g., when actuation structure 120 is fully decompressed. Actuation ring 130 may be configured to extend a second distance from actuation structure proximal end 122, e.g., due to a compression of actuation structure 120. Illustratively, the second distance from actuation structure proximal end 122 may be greater than the first distance from actuation structure proximal end 122.

FIG. 1B illustrates a cross-sectional view of handle 100. In one or more embodiments, handle 100 may comprise an inner bore 140, an inner bore proximal taper 150, a piston tube housing 160, and a fixation mechanism housing 170. Handle 100 may be manufactured from any suitable material, e.g., polymers, metals, metal alloys, etc., or from any combination of suitable materials.

FIG. 2 is a schematic diagram illustrating an exploded view of a steerable laser probe assembly 200. In one or more embodiments, steerable laser probe assembly 200 may comprise a handle 100, a fixation mechanism 210, a nosecone fixation mechanism 215, a piston tube 220 having a piston tube distal end 221 and a piston tube proximal end 222, an outer nosecone 230 having an outer nosecone distal end 231 and an outer nosecone proximal end 232, an inner nosecone 240 having an inner nosecone distal end 241 and an inner nosecone proximal end 242, an optic fiber 250 having an optic fiber distal end 251 and an optic fiber proximal end 252, a flexible housing tube 260 having a flexible housing tube distal end 261 and a flexible housing tube proximal end 262, and a light source interface 270. Illustratively, light source interface 270 may be configured to interface with optic fiber 250, e.g., at optic fiber proximal end 252. In one or more embodiments, light source interface 270 may comprise a standard light source connecter, e.g., an SMA connector.

In one or more embodiments, a portion of piston tube 220 may be disposed within piston tube housing 160, e.g., piston tube proximal end 222 may be disposed within piston tube housing 160. Illustratively, piston tube 220 may be fixed to outer nosecone 230, e.g., piston tube distal end 221 may be fixed to outer nosecone proximal end 232. In one or more embodiments, a portion of piston tube 220 may be disposed within a portion of outer nosecone 230, e.g., piston tube distal end 221 may be disposed within outer nosecone 230. Illustratively, a portion of piston tube 220 may be disposed within a portion of outer nosecone 230 wherein piston tube 220 is fixed to outer nosecone 230. In one or more embodiments, piston tube 220 may be fixed to outer nosecone 230, e.g., by an adhesive or any suitable fixation means. Illustratively, piston tube 220 and outer nosecone 230 may be manufactured as a single unit. Piston tube 220 and outer nosecone 230 may be manufactured from any suitable material, e.g., polymers, metals, metal alloys, etc., or from any combination of suitable materials.

Illustratively, inner nosecone 240 may be fixed to outer nosecone 230, e.g., inner nosecone proximal end 242 may be fixed to outer nosecone distal end 231. In one or more embodiments, a portion of inner nosecone 240 may be disposed within a portion of outer nosecone 230, e.g., inner nosecone proximal end 242 may be disposed within outer nosecone 230. Illustratively, a portion of inner nosecone 240 may be disposed within a portion of outer nosecone 230 wherein inner nosecone 240 is fixed to outer nosecone 230. In one or more embodiments, inner nosecone 240 may be fixed to outer nosecone 230, e.g., by an adhesive or any suitable fixation means. Illustratively, nosecone fixation mechanism 215 may be configured to fix inner nosecone 240 to outer nosecone 230. For example, nosecone fixation mechanism 215 may comprise a set screw configured to firmly attach inner nosecone 240 to outer nosecone 230. In one or more embodiments, inner nosecone 240 and outer nosecone 230 may be manufactured as a single unit Inner nosecone 240 and outer nosecone 230 may be manufactured from any suitable material, e.g., polymers, metals, metal alloys, etc., or from any combination of suitable materials.

Illustratively, outer nosecone 230 may be fixed to actuation structure 120, e.g., outer nosecone proximal end 232 may be fixed to handle distal end 101. In one or more embodiments, a portion of outer nosecone 230 may be disposed within actuation ring 130, e.g., outer nosecone proximal end 232 may be disposed within actuation ring 130. Illustratively, a portion of outer nosecone 230 may be disposed within actuation ring 130 wherein outer nosecone 230 is fixed to actuation ring 130. In one or more embodiments, outer nosecone 230 may be fixed to actuation structure 120, e.g., by an adhesive or any suitable fixation means.

Illustratively, a portion of flexible housing tube 260 may be fixed to inner nosecone 240, e.g., flexible housing tube proximal end 262 may be fixed to inner nosecone distal end 241. In one or more embodiments, a portion of flexible housing tube 260 may be fixed to inner nosecone 240, e.g., by an adhesive or any suitable fixation means. Illustratively, a portion of flexible housing tube 260 may be disposed within a portion of inner nosecone 240, e.g., flexible housing tube proximal end 262 may be disposed within a portion of inner nosecone 240. In one or more embodiments, a portion of flexible housing tube 260 may be fixed within inner nosecone 240, e.g., by an adhesive or any suitable fixation means. Flexible housing tube 260 may be manufactured from any suitable material, e.g., polymers, metals, metal alloys, etc., or from any combination of suitable materials. Illustratively, flexible housing tube 260 may comprise a shape memory material, e.g., Nitinol. In one or more embodiments, flexible housing tube 260 may be manufactured from a material having an ultimate tensile strength between 700 and 1000 MPa. Illustratively, flexible housing tube 260 may be manufactured from a material having ultimate tensile strength less than 700 MPa or greater than 1000 MPa. In one or more embodiments, flexible housing tube 260 may be manufactured from a material having a modulus of elasticity between 30 and 80 GPa. Illustratively, flexible housing tube 260 may be manufactured from a material having a modulus of elasticity less than 30 GPa or greater than 80 GPa.

In one or more embodiments, flexible housing tube 260 may be manufactured with dimensions suitable for performing microsurgical procedures, e.g., ophthalmic surgical procedures. Illustratively, flexible housing tube 260 may be manufactured at gauge sizes commonly used in ophthalmic surgical procedures, e.g., 23 gauge, 25 gauge, etc. In one or more embodiments, flexible housing tube 260 may be configured to be inserted in a cannula, e.g., a cannula used during an ophthalmic surgical procedure. For example, one or more properties of flexible housing tube 260 may be optimized to reduce friction as flexible housing tube 260 is inserted into a cannula. In one or more embodiments, one or more properties of flexible housing tube 260 may be optimized to reduce friction as flexible housing tube 260 is removed from a cannula. Illustratively, flexible housing tube 260 may have an ultimate tensile strength between 1000 MPa and 1100 MPa. In one or more embodiments, flexible housing tube 260 may have an ultimate tensile strength less than 1000 MPa or greater than 1100 MPa.

In one or more embodiments, optic fiber 250 may be disposed within inner bore 140, fixation mechanism housing 170, piston tube housing 160, piston tube 220, outer nosecone 230, inner nosecone 240, and flexible housing tube 260. Illustratively, optic fiber 250 may be disposed within flexible housing tube 260 wherein optic fiber distal end 251 is adjacent to flexible housing tube distal end 261. In one or more embodiments, a portion of optic fiber 250 may be fixed to a portion of flexible housing tube 260, e.g., by an adhesive or any suitable fixation means. Illustratively, fixation mechanism 210 may be disposed within fixation mechanism housing 170. In one or more embodiments, fixation mechanism 210 may be configured to fix a portion of optic fiber 250 in a position relative to handle base 110. Illustratively, fixation mechanism 210 may comprise a set screw configured to fix a portion of optic fiber 250 in a position relative to handle base 110, e.g., by a press fit or any suitable fixation means. In one or more embodiments, a portion of optic fiber 250 may be fixed to a portion of fixation mechanism 210, e.g., by an adhesive or any suitable fixation means. Illustratively, optic fiber 250 may be fixed in a position relative to handle base 110 and fixed to a portion of flexible housing tube 260.

In one or more embodiments, a compression of actuation structure 120 may be configured to extend actuation ring 130 relative to handle proximal end 102. Illustratively, an extension of actuation ring 130 relative to handle proximal end 102 may be configured to extend piston tube 220, outer nosecone 230, inner nosecone 240, and flexible housing tube 260 relative to handle proximal end 102. In one or more embodiments, an extension of flexible housing tube 260 relative to handle proximal end 102 may be configured to extend flexible housing tube 260 relative to optic fiber 250. Illustratively, a compression of actuation structure 120 may be configured to extend flexible housing tube 260 relative to optic fiber 250. In one or more embodiments, a portion of optic fiber 250 may be configured to resist an extension of flexible housing tube 260, e.g., a portion of optic fiber 250 that is fixed to flexible housing tube 260 may be configured to resist an extension of flexible housing tube 260 relative to handle proximal end 102. Illustratively, as flexible housing tube 260 is extended relative to optic fiber 250, e.g., due to a compression of actuation structure 120, optic fiber 250 may be configured to provide a resistive force, e.g., to resist an extension of a portion of flexible housing tube 260 relative to handle proximal end 102. In one or more embodiments, as flexible housing tube 260 is extended relative to handle proximal end 102, optic fiber 250 may be configured to apply a compressive force to a portion of flexible housing tube 260. Illustratively, an application of a compressive or a resistive force to a portion of flexible housing tube 260 may be configured to compress a portion of flexible housing tube 260. In one or more embodiments, a compression of a portion of flexible housing tube 260 may be configured to cause flexible housing tube 260 to gradually curve. Illustratively, a gradual curving of flexible housing tube 260 may be configured to gradually curve optic fiber 250.

In one or more embodiments, a compression of actuation structure 120 may be configured to gradually curve optic fiber 250. Illustratively, a compression of actuation structure 120 may be configured to curve optic fiber 250 wherein a line tangent to optic fiber distal end 251 and a line tangent to optic fiber proximal end 252 may intersect at a curved optic fiber angle. In one or more embodiments, a compression of actuation structure 120 may be configured to curve flexible housing tube 260 wherein a line tangent to flexible housing tube distal end 261 may intersect a line tangent to flexible housing tube proximal end 262 at a curved flexible housing tube angle. Illustratively, a particular compression of actuation structure 120 may be configured to cause the curved optic fiber angle and the curved flexible housing tube angle to be equal, e.g., when optic fiber 250 is fixed to flexible housing tube 260 at a single fixation point. In one or more embodiments, a particular compression of actuation structure 120 may be configured to cause the curved optic fiber angle to be no more than 1.0 degrees less than the curved flexible housing tube angle, e.g., when optic fiber 250 is fixed to flexible housing tube 260 at a single fixation point. Illustratively, optic fiber 250 may comprise a majority of the area inside flexible housing tube 260.

In one or more embodiments, a decompression of actuation structure 120 may be configured to retract actuation ring 130 relative to handle proximal end 102. Illustratively, a retraction of actuation ring 130 relative to handle proximal end 102 may be configured to retract piston tube 220, outer nosecone 230, inner nosecone 240, and flexible housing tube 260 relative to handle proximal end 102. In one or more embodiments, a refraction of flexible housing tube 260 relative to handle proximal end 102 may be configured to retract flexible housing tube 260 relative to optic fiber 250. Illustratively, a decompression of actuation structure 120 may be configured to retract flexible housing tube 260 relative to optic fiber 250. In one or more embodiments, a portion of optic fiber 250 may be configured to facilitate a retraction of flexible housing tube 260, e.g., a portion of optic fiber 250 that is fixed to flexible housing tube 260 may be configured to facilitate a retraction of a portion of flexible housing tube 260 relative to handle proximal end 102. Illustratively, as flexible housing tube 260 is retracted relative to optic fiber 250, e.g., due to a decompression of actuation structure 120, optic fiber 250 may be configured to reduce a resistive force, e.g., to facilitate a retraction of flexible housing tube 260 relative to handle proximal end 102. In one or more embodiments, as flexible housing tube 260 is refracted relative to handle proximal end 102, optic fiber 250 may be configured to reduce a compressive force applied to a portion of flexible housing tube 260. Illustratively, a reduction of a compressive or a resistive force applied to a portion of flexible housing tube 260 may be configured to decompress a portion of flexible housing tube 260. In one or more embodiments, a decompression of a portion of flexible housing tube 260 may be configured to cause flexible housing tube 260 to gradually straighten. Illustratively, a gradual straightening of flexible housing tube 260 may be configured to gradually straighten optic fiber 250.

In one or more embodiments, a decompression of actuation structure 120 may be configured to gradually straighten optic fiber 250. Illustratively, a decompression of actuation structure 120 may be configured to straighten optic fiber 250 wherein a line tangent to optic fiber distal end 251 and a line tangent to optic fiber proximal end 252 may intersect at a straightened optic fiber angle. In one or more embodiments, a decompression of actuation structure 120 may be configured to straighten flexible housing tube 260 wherein a line tangent to flexible housing tube distal end 261 may intersect a line tangent to flexible housing tube proximal end 262 at a straightened flexible housing tube angle. Illustratively, a particular decompression of actuation structure 120 may be configured to cause the straightened optic fiber angle and the straightened flexible housing tube angle to be equal, e.g., when optic fiber 250 is fixed to flexible housing tube 260 at a single fixation point. In one or more embodiments, a particular decompression of actuation structure 120 may be configured to cause the straightened optic fiber angle to be no more than 1.0 degrees less than the straightened flexible housing tube angle, e.g., when optic fiber 250 is fixed to flexible housing tube 260 at a single fixation point.

FIGS. 3A, 3B, 3C, 3D, and 3E illustrate a gradual curving of an optic fiber 250. FIG. 3A illustrates a straight optic fiber 300. In one or more embodiments, optic fiber 250 may comprise a straight optic fiber 300, e.g., when flexible housing tube 260 is fully refracted relative to handle proximal end 102. Illustratively, optic fiber 250 may comprise a straight optic fiber 300, e.g., when actuation structure 120 is fully decompressed. In one or more embodiments, optic fiber 250 may comprise a straight optic fiber 300, e.g., when actuation ring 130 is fully retracted relative to handle proximal end 102. Illustratively, a line tangent to optic fiber distal end 251 may be parallel to a line tangent to flexible housing tube proximal end 262, e.g., when optic fiber 250 comprises a straight optic fiber 300.

Figure 3B:
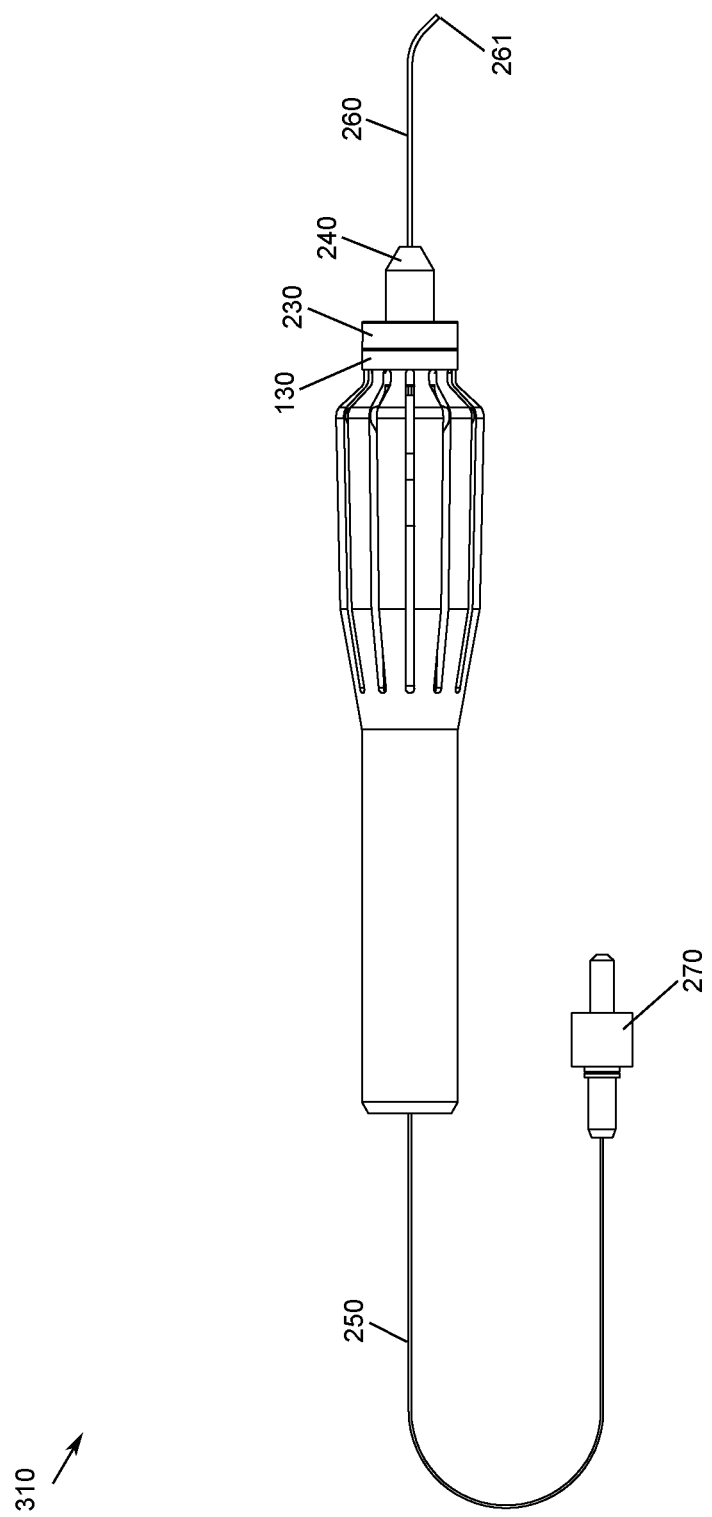

FIG. 3B illustrates an optic fiber in a first curved position 310. In one or more embodiments, a compression of actuation structure 120 may be configured to gradually curve optic fiber 250 from a straight optic fiber 300 to an optic fiber in a first curved position 310. Illustratively, a compression of actuation structure 120 may be configured to extend actuation ring 130 relative to handle proximal end 102. In one or more embodiments, an extension of actuation ring 130 relative to handle proximal end 102 may be configured to extend flexible housing tube 260 relative to optic fiber 250. Illustratively, an extension of flexible housing tube 260 relative to optic fiber 250 may be configured to apply a force to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to resist an extension of flexible housing tube 260 relative to optic fiber 250. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from a straight optic fiber 300 to an optic fiber in a first curved position 310. Illustratively, a line tangent to optic fiber distal end 251 may intersect a line tangent to flexible housing tube proximal end 262 at a first angle, e.g., when optic fiber 250 comprises an optic fiber in a first curved position 310. In one or more embodiments, the first angle may comprise any angle greater than zero degrees. For example, the first angle may comprise a 45 degree angle.

Figure 3C:
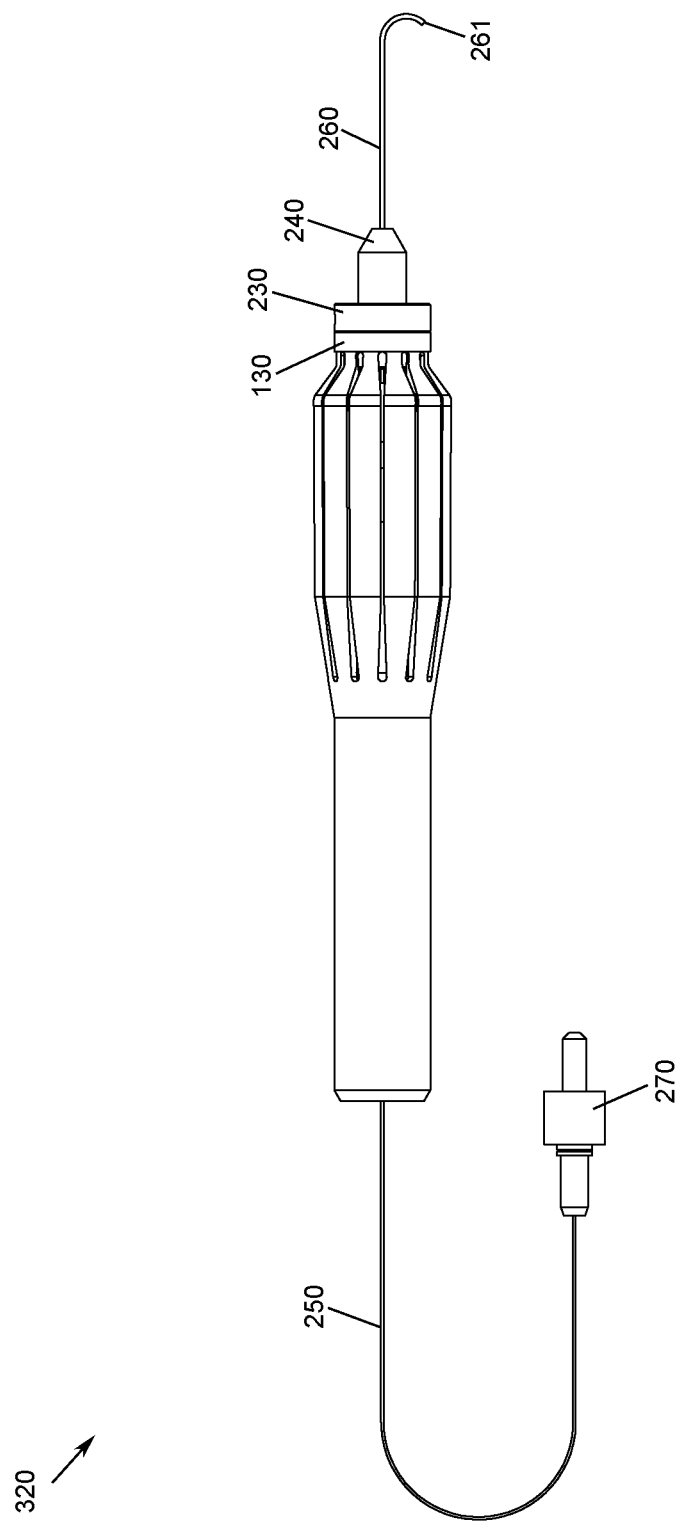

FIG. 3C illustrates an optic fiber in a second curved position 320. In one or more embodiments, a compression of actuation structure 120 may be configured to gradually curve optic fiber 250 from an optic fiber in a first curved position 310 to an optic fiber in a second curved position 320. Illustratively, a compression of actuation structure 120 may be configured to extend actuation ring 130 relative to handle proximal end 102. In one or more embodiments, an extension of actuation ring 130 relative to handle proximal end 102 may be configured to extend flexible housing tube 260 relative to optic fiber 250. Illustratively, an extension of flexible housing tube 260 relative to optic fiber 250 may be configured to apply a force to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to resist an extension of flexible housing tube 260 relative to optic fiber 250. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from an optic fiber in a first curved position 310 to an optic fiber in a second curved position 320. Illustratively, a line tangent to optic fiber distal end 251 may intersect a line tangent to flexible housing tube proximal end 262 at a second angle, e.g., when optic fiber 250 comprises an optic fiber in a second curved position 320. In one or more embodiments, the second angle may comprise any angle greater than the first angle. For example, the second angle may comprise a 90 degree angle.

Figure 3D:
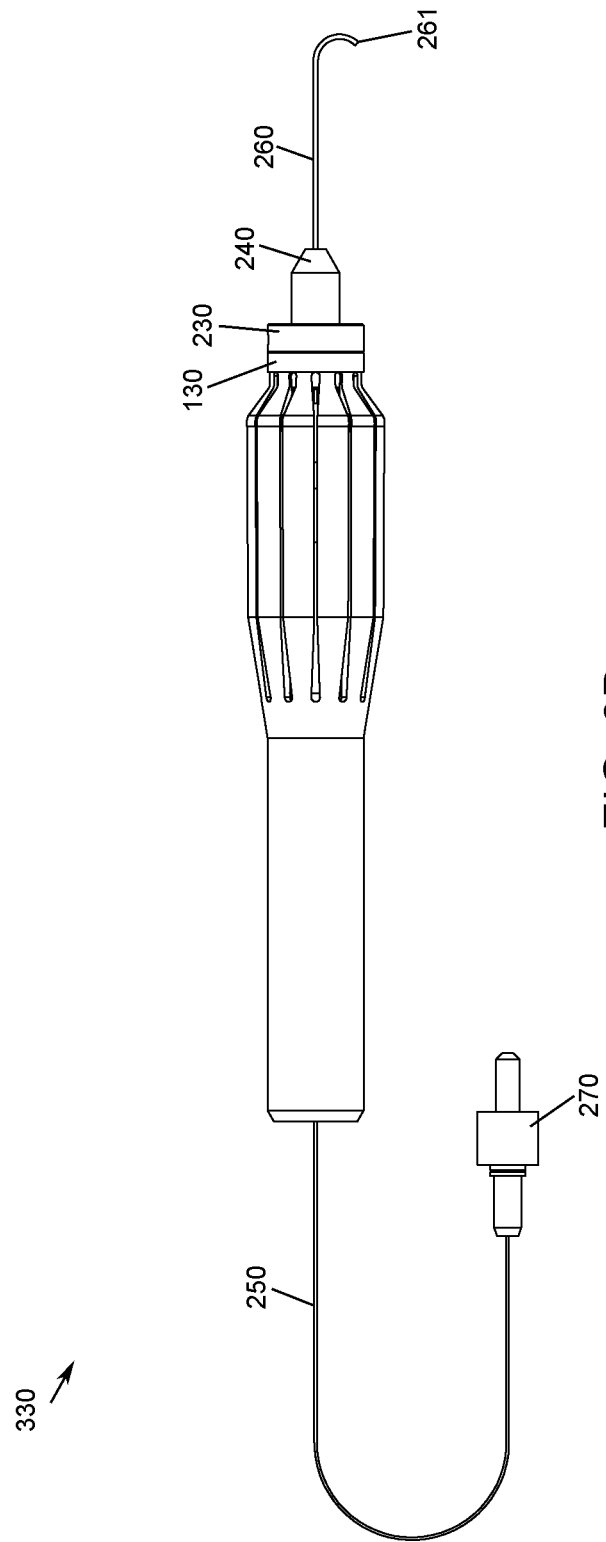

FIG. 3D illustrates an optic fiber in a third curved position 330. In one or more embodiments, a compression of actuation structure 120 may be configured to gradually curve optic fiber 250 from an optic fiber in a second curved position 320 to an optic fiber in a third curved position 330. Illustratively, a compression of actuation structure 120 may be configured to extend actuation ring 130 relative to handle proximal end 102. In one or more embodiments, an extension of actuation ring 130 relative to handle proximal end 102 may be configured to extend flexible housing tube 260 relative to optic fiber 250. Illustratively, an extension of flexible housing tube 260 relative to optic fiber 250 may be configured to apply a force to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to resist an extension of flexible housing tube 260 relative to optic fiber 250. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from an optic fiber in a second curved position 320 to an optic fiber in a third curved position 330. Illustratively, a line tangent to optic fiber distal end 251 may intersect a line tangent to flexible housing tube proximal end 262 at a third angle, e.g., when optic fiber 250 comprises an optic fiber in a third curved position 330. In one or more embodiments, the third angle may comprise any angle greater than the second angle. For example, the third angle may comprise a 135 degree angle.

Figure 3E:
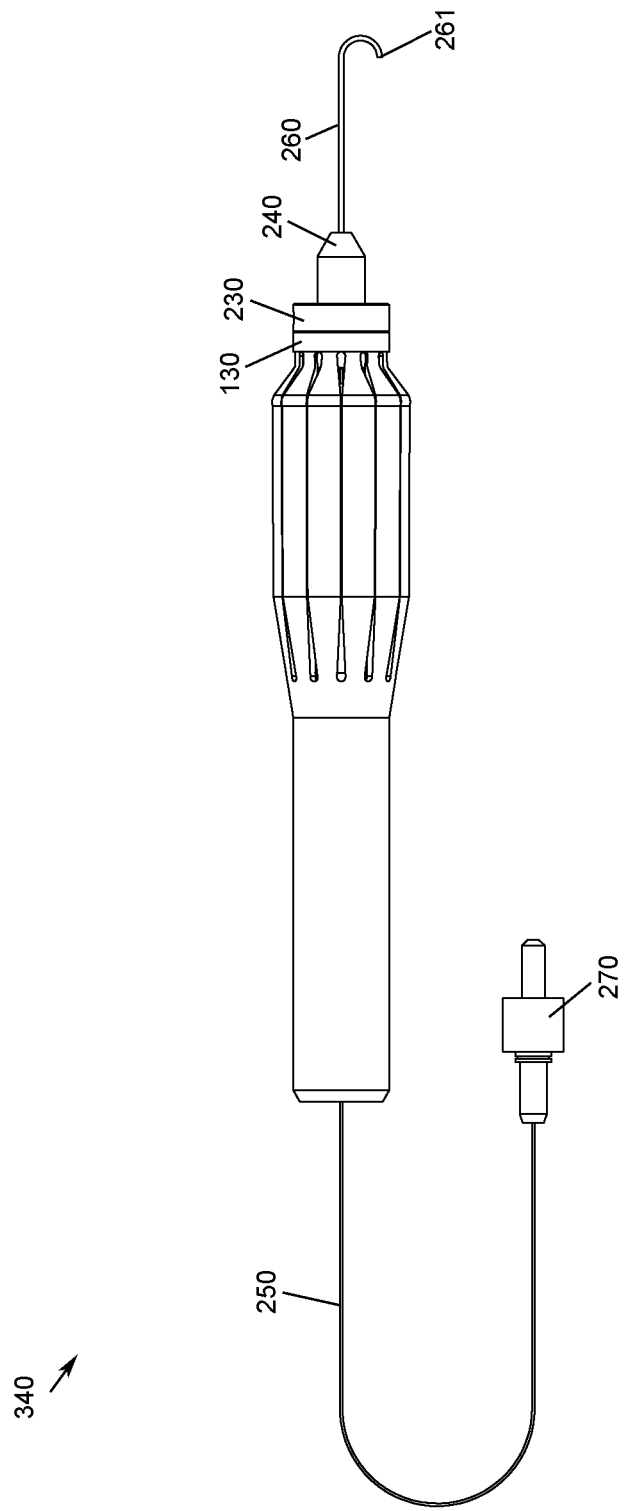

FIG. 3E illustrates an optic fiber in a fourth curved position 340. In one or more embodiments, a compression of actuation structure 120 may be configured to gradually curve optic fiber 250 from an optic fiber in a third curved position 330 to an optic fiber in a fourth curved position 340. Illustratively, a compression of actuation structure 120 may be configured to extend actuation ring 130 relative to handle proximal end 102. In one or more embodiments, an extension of actuation ring 130 relative to handle proximal end 102 may be configured to extend flexible housing tube 260 relative to optic fiber 250. Illustratively, an extension of flexible housing tube 260 relative to optic fiber 250 may be configured to apply a force to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to resist an extension of flexible housing tube 260 relative to optic fiber 250. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from an optic fiber in a third curved position 330 to an optic fiber in a fourth curved position 340. Illustratively, a line tangent to optic fiber distal end 251 may be parallel to a line tangent to flexible housing tube proximal end 262, e.g., when optic fiber 250 comprises an optic fiber in a fourth curved position 340.

In one or more embodiments, one or more properties of a steerable laser probe may be adjusted to attain one or more desired steerable laser probe features. For example, a length that flexible housing tube distal end 261 extends from inner nosecone distal end 241 may be adjusted to vary an amount of compression of actuation structure 120 configured to curve flexible housing tube 260 to a particular curved position. In one or more embodiments, a stiffness of flexible housing tube 260 may be adjusted to vary an amount of compression of actuation structure 120 configured to curve flexible housing tube 260 to a particular curved position. Illustratively, a material comprising flexible housing tube 260 may be adjusted to vary an amount of compression of actuation structure 120 configured to curve flexible housing tube 260 to a particular curved position. In one or more embodiments, a stiffness of flexible housing tube 260 may be adjusted to vary a bend radius of flexible housing tube 260. For example, a stiffness of flexible housing tube 260 may be adjusted to vary a radius of curvature of flexible housing tube 260, e.g., when flexible housing tube 260 is in a particular curved position.

Illustratively, a distance that inner nosecone distal end 241 extends from outer nosecone distal end 231 may be adjusted to vary an amount of compression of actuation structure 120 configured to curve flexible housing tube 260 to a particular curved position. For example, an amount of compression of actuation structure 120 configured to curve flexible housing tube 260 to a particular curved position may be reduced, e.g., by increasing a distance that inner nosecone distal end 241 extends from outer nosecone distal end 231. In one or more embodiments, an amount of compression of actuation structure 120 configured to curve flexible housing tube 260 to a particular curved position may be increased, e.g., by decreasing a distance that inner nosecone distal end 241 extends from outer nosecone distal end 231. Illustratively, a steerable laser probe may comprise a mechanism configured to allow a surgeon or a surgeon's assistant to adjust a distance that inner nosecone distal end 241 extends from outer nosecone distal end 231. For example, a mechanism may be configured to expand or collapse a portion of nosecone fixation mechanism 215. In one or more embodiments, an expansion of a portion of nosecone fixation mechanism 215 may be configured to increase a distance that inner nosecone distal end 241 extends from outer nosecone distal end 231. Illustratively, a collapse of a portion of nosecone fixation mechanism 215 may be configured to decrease a distance that inner nosecone distal end 241 extends from outer nosecone distal end 231.

In one or more embodiments, a geometry of actuation structure 120 may be adjusted to vary an amount of compression of actuation structure 120 configured to curve flexible housing tube 260 to a particular curved position. Illustratively, one or more locations within flexible housing tube 260 wherein optic fiber 250 may be fixed to an inner portion of flexible housing tube 260 may be adjusted to vary an amount of compression of actuation structure 120 configured to curve flexible housing tube 260 to a particular curved position. In one or more embodiments, at least a portion of optic fiber 250 may be enclosed in an optic fiber sleeve configured to, e.g., protect optic fiber 250, vary a stiffness of optic fiber 250, vary an optical property of optic fiber 250, etc.

Illustratively, an optic fiber sleeve may be configured to compress a portion of flexible housing tube 260. For example, an optic fiber sleeve may enclose a portion of optic fiber 250 and the optic fiber sleeve may be fixed in a position relative to handle base 110, e.g., fixation mechanism 210 may be configured to fix the optic fiber sleeve in a position relative to handle base 110. Illustratively, a portion of the optic fiber sleeve may be fixed to a portion of flexible housing tube 260, e.g., by an adhesive or any suitable fixation means. In one or more embodiments, a compression of actuation structure 120 may be configured to extend flexible housing tube 260 relative to an optic fiber sleeve. Illustratively, an extension of flexible housing tube 260 relative to an optic fiber sleeve may be configured to cause the optic fiber sleeve to apply a force, e.g., a compressive force, to a portion of flexible housing tube 260 causing flexible housing tube 260 to gradually curve. In one or more embodiments, a gradual curving of flexible housing tube 260 may be configured to gradually curve optic fiber 250.

Illustratively, a steerable laser probe may be configured to indicate, e.g., to a surgeon, a direction that optic fiber 250 may curve, e.g., due to a compression of actuation structure 120. In one or more embodiments, a portion of a steerable laser probe, e.g., handle 100, may be marked in a manner configured to indicate a direction that optic fiber 250 may curve. For example, a portion of flexible housing tube 260 may comprise a mark configured to indicate a direction that optic fiber 250 may curve. Illustratively, flexible housing tube 260 may comprise a slight curve, e.g., a curve less than 7.5 degrees, when actuation structure 120 is fully decompressed. In one or more embodiments, flexible housing tube 260 may comprise a slight curve configured to indicate a direction that optic fiber 250 may curve, e.g., due to a compression of actuation structure 120. Illustratively, a steerable laser probe may comprise a mechanism configured to allow a surgeon or a surgeon's assistant to adjust a degree of a slight curve in flexible housing tube 260. For example, a steerable laser probe may comprise a mechanism configured to expand or collapse nosecone fixation mechanism 215.

Figure 4A:
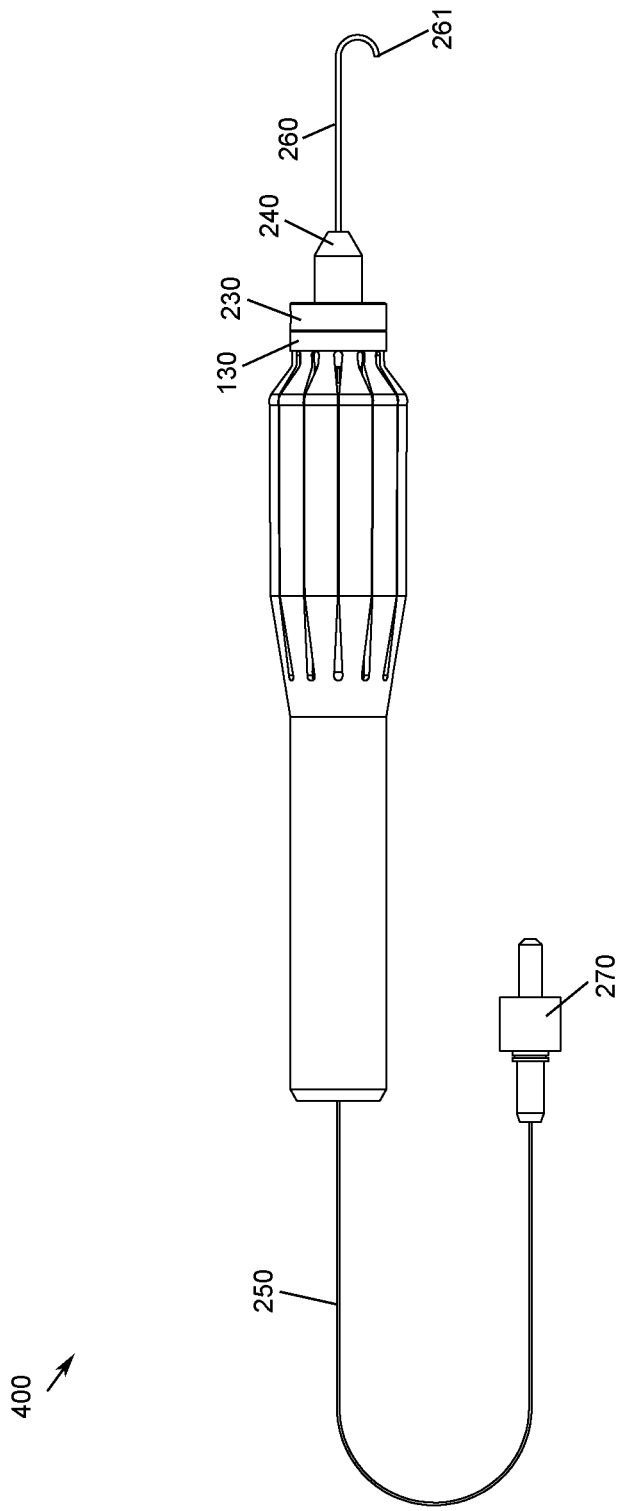
FIGS. 4A, 4B, 4C, 4D, and 4E illustrate a gradual straightening of an optic fiber.

FIGS. 4A, 4B, 4C, 4D, and 4E illustrate a gradual straightening of an optic fiber 250. FIG. 4A illustrates a fully curved optic fiber 400. In one or more embodiments, optic fiber 250 may comprise a fully curved optic fiber 400, e.g., when flexible housing tube 260 is fully extended relative to optic fiber 250. For example, optic fiber 250 may comprise a fully curved optic fiber 400 when actuation ring 130 is fully extended relative to handle proximal end 102. Illustratively, optic fiber 250 may comprise a fully curved optic fiber 400, e.g., when a portion of flexible housing tube 260 is compressed. In one or more embodiments, optic fiber 250 may comprise a fully curved optic fiber 400, e.g., when actuation structure 120 is fully compressed. Illustratively, a line tangent to optic fiber distal end 251 may be parallel to a line tangent to flexible housing tube proximal end 262, e.g., when optic fiber 250 comprises a fully curved optic fiber 400.

Figure 4B:
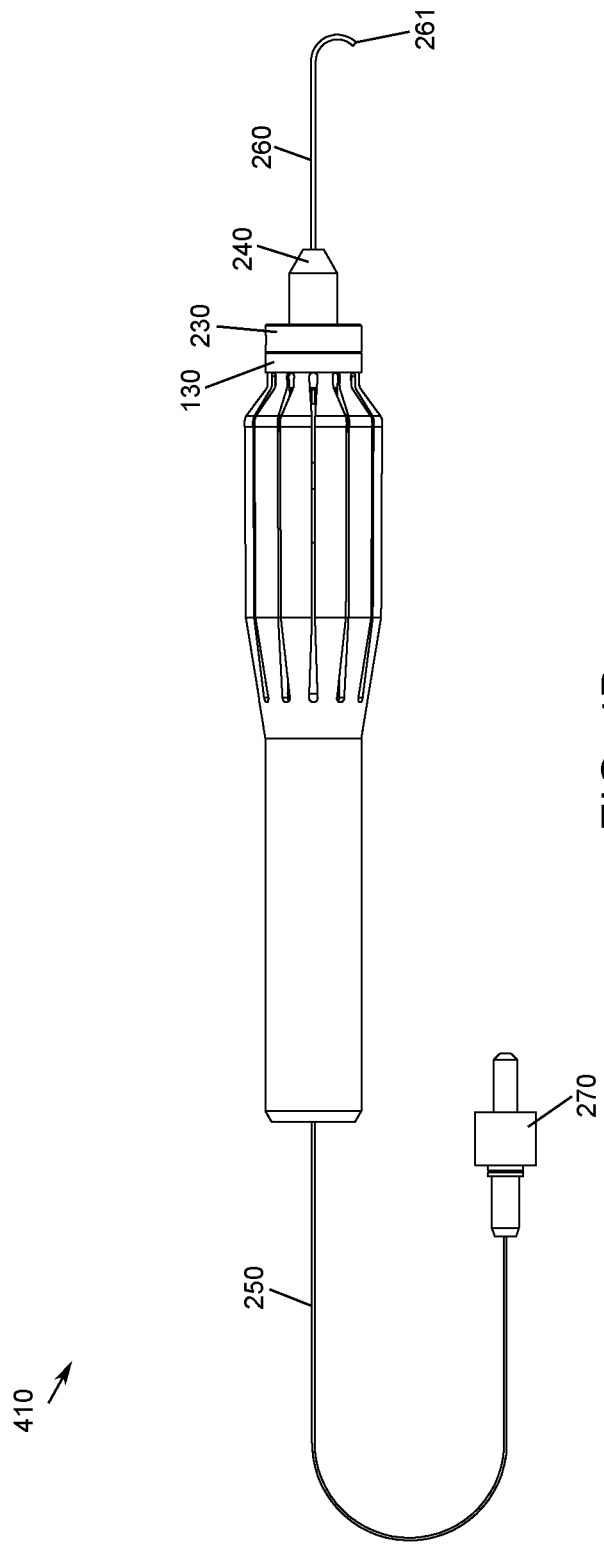

FIG. 4B illustrates an optic fiber in a first partially straightened position 410. In one or more embodiments, a decompression of actuation structure 120 may be configured to gradually straighten optic fiber 250 from a fully curved optic fiber 400 to an optic fiber in a first partially straightened position 410. Illustratively, a decompression of actuation structure 120 may be configured to retract actuation ring 130 relative to handle proximal end 102. In one or more embodiments, a retraction of actuation ring 130 relative to handle proximal end 102 may be configured to retract flexible housing tube 260 relative to optic fiber 250. Illustratively, a refraction of flexible housing tube 260 relative to optic fiber 250 may be configured to reduce a force applied to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to facilitate a retraction of flexible housing tube 260 relative to optic fiber 250. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from a fully curved optic fiber 400 to an optic fiber in a first partially straightened position 410. Illustratively, a line tangent to optic fiber distal end 251 may intersect a line tangent to flexible housing tube proximal end 262 at a first partially straightened angle, e.g., when optic fiber 250 comprises an optic fiber in a first partially straightened position 410. In one or more embodiments, the first partially straightened angle may comprise any angle less than 180 degrees. For example, the first partially straightened angle may comprise a 135 degree angle.

Figure 4C:
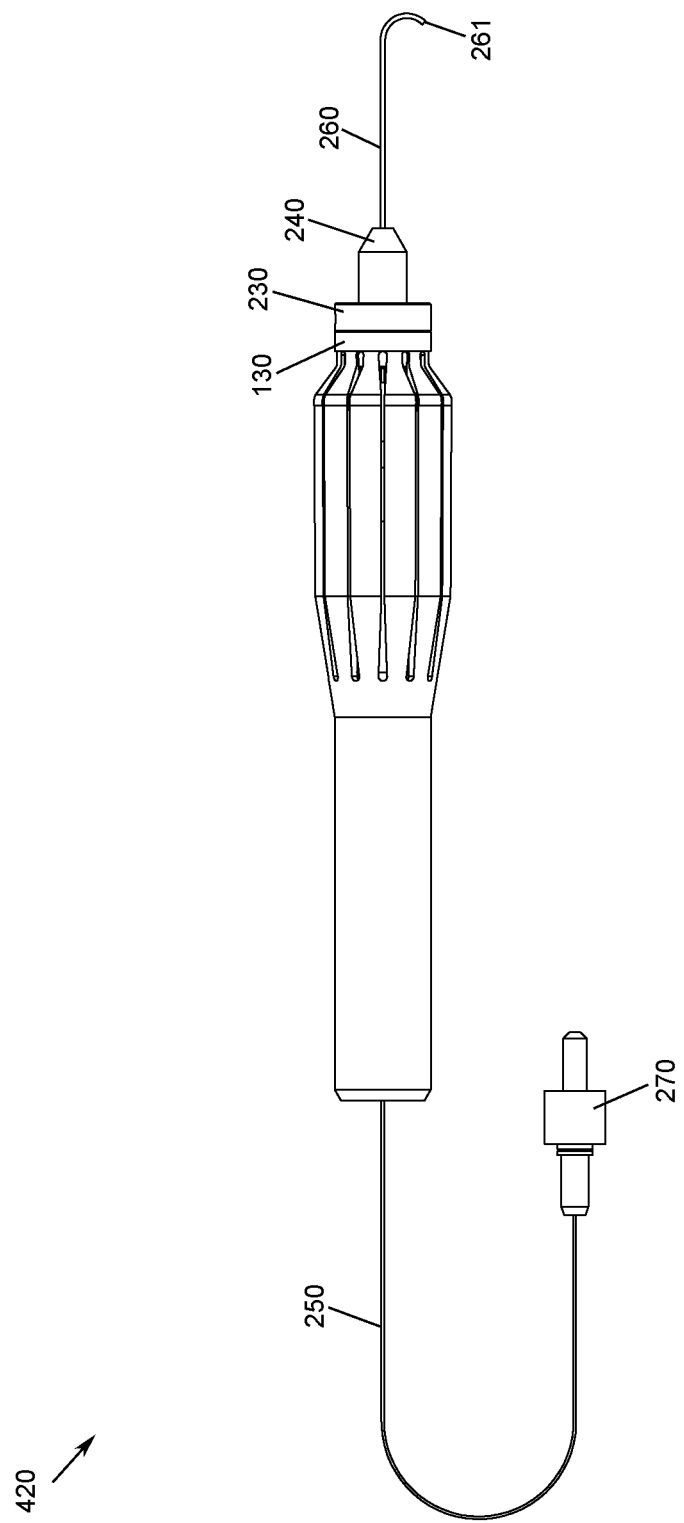

FIG. 4C illustrates an optic fiber in a second partially straightened position 420. In one or more embodiments, a decompression of actuation structure 120 may be configured to gradually straighten optic fiber 250 from an optic fiber in a first partially straightened position 410 to an optic fiber in a second partially straightened position 420. Illustratively, a decompression of actuation structure 120 may be configured to retract actuation ring 130 relative to handle proximal end 102. In one or more embodiments, a retraction of actuation ring 130 relative to handle proximal end 102 may be configured to retract flexible housing tube 260 relative to optic fiber 250. Illustratively, a retraction of flexible housing tube 260 relative to optic fiber 250 may be configured to reduce a force applied to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to facilitate a retraction of flexible housing tube 260 relative to optic fiber 250. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from an optic fiber in a first partially straightened position 410 to an optic fiber in a second partially straightened position 420. Illustratively, a line tangent to optic fiber distal end 251 may intersect a line tangent to flexible housing tube proximal end 262 at a second partially straightened angle, e.g., when optic fiber 250 comprises an optic fiber in a second partially straightened position 420. In one or more embodiments, the second partially straightened angle may comprise any angle less than the first partially straightened angle. For example, the second partially straightened angle may comprise a 90 degree angle.

Figure 4D:
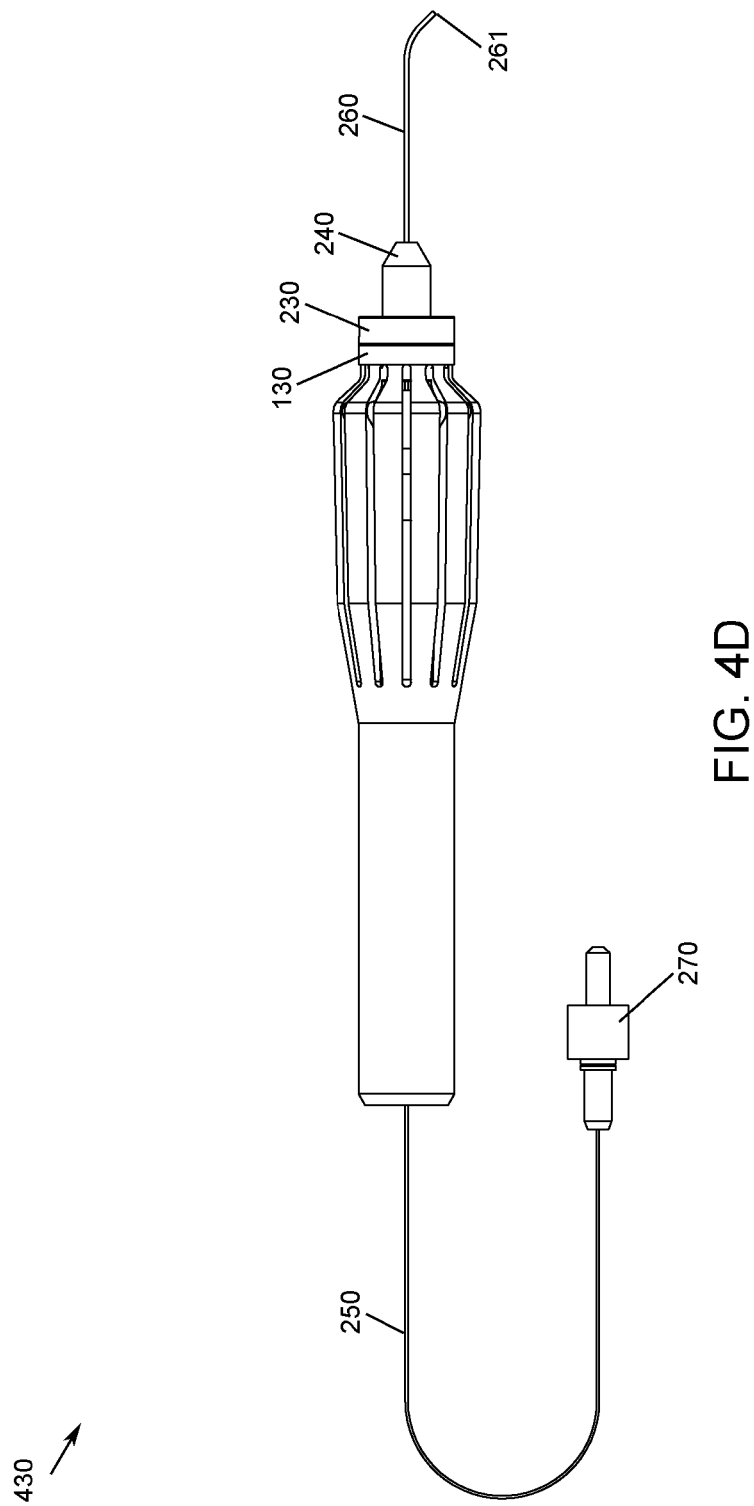

FIG. 4D illustrates an optic fiber in a third partially straightened position 430. In one or more embodiments, a decompression of actuation structure 120 may be configured to gradually straighten optic fiber 250 from an optic fiber in a second partially straightened position 420 to an optic fiber in a third partially straightened position 430. Illustratively, a decompression of actuation structure 120 may be configured to retract actuation ring 130 relative to handle proximal end 102. In one or more embodiments, a retraction of actuation ring 130 relative to handle proximal end 102 may be configured to retract flexible housing tube 260 relative to optic fiber 250. Illustratively, a retraction of flexible housing tube 260 relative to optic fiber 250 may be configured to reduce a force applied to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to facilitate a retraction of flexible housing tube 260 relative to optic fiber 250. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from an optic fiber in a second partially straightened position 420 to an optic fiber in a third partially straightened position 430. Illustratively, a line tangent to optic fiber distal end 251 may intersect a line tangent to flexible housing tube proximal end 262 at a third partially straightened angle, e.g., when optic fiber 250 comprises an optic fiber in a third partially straightened position 430. In one or more embodiments, the third partially straightened angle may comprise any angle less than the second partially straightened angle. For example, the third partially straightened angle may comprise a 45 degree angle.

Figure 4E:
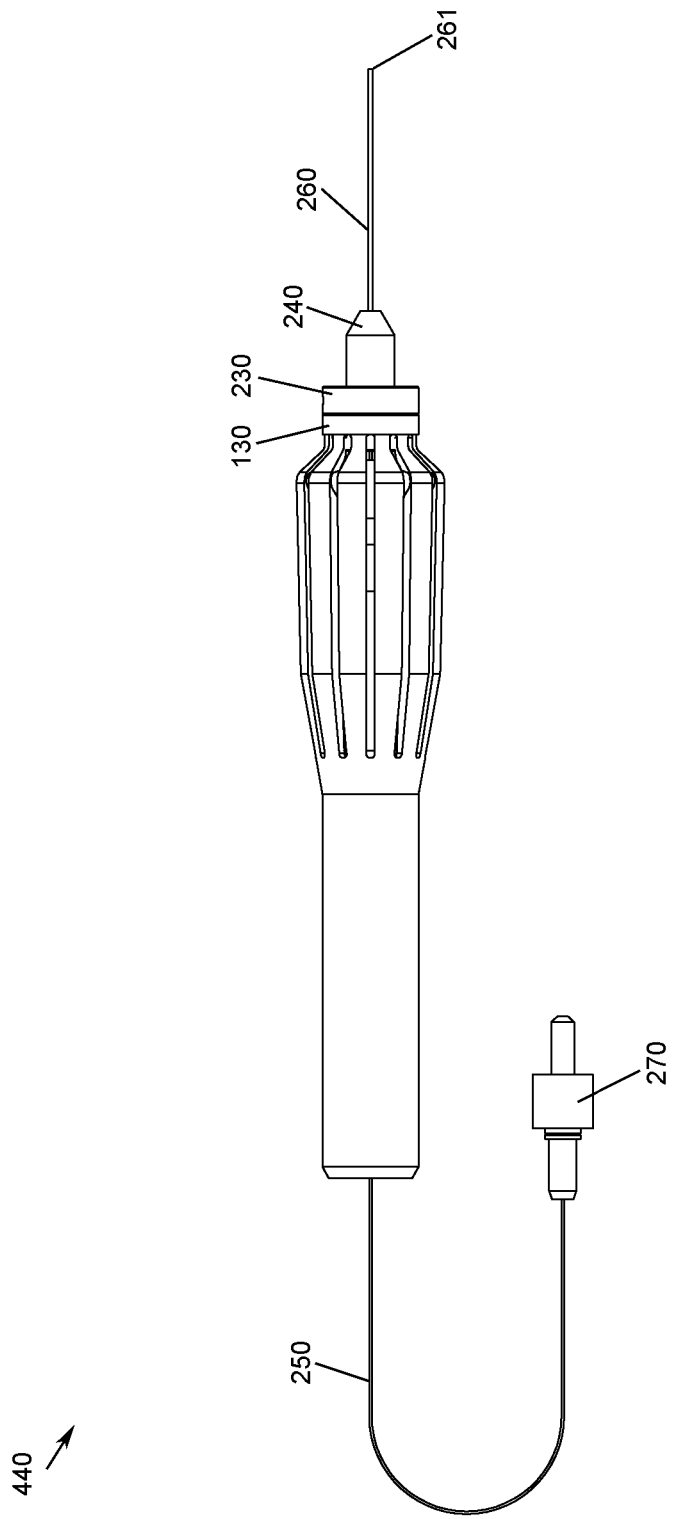

FIG. 4E illustrates an optic fiber in a fully straightened position 440. In one or more embodiments, a decompression of actuation structure 120 may be configured to gradually straighten optic fiber 250 from an optic fiber in a third partially straightened position 430 to an optic fiber in a fully straightened position 440. Illustratively, a decompression of actuation structure 120 may be configured to retract actuation ring 130 relative to handle proximal end 102. In one or more embodiments, a retraction of actuation ring 130 relative to handle proximal end 102 may be configured to retract flexible housing tube 260 relative to optic fiber 250. Illustratively, a retraction of flexible housing tube 260 relative to optic fiber 250 may be configured to reduce a force applied to a portion of flexible housing tube 260. In one or more embodiments, optic fiber 250 may be fixed in a position relative to handle base 110 and optic fiber 250 may also be fixed to a portion of flexible housing tube 260. For example, a portion of optic fiber 250 may be configured to facilitate a retraction of flexible housing tube 260 relative to optic fiber 250. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from an optic fiber in a third partially straightened position 430 to an optic fiber in a fully straightened position 440. Illustratively, a line tangent to optic fiber distal end 251 may be parallel to a line tangent to flexible housing tube proximal end 262, e.g., when optic fiber 250 comprises an optic fiber in a fully straightened position 440.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient flexible housing tube 260 in an orientation configured to cause a curvature of flexible housing tube 260 within the particular transverse plane of the inner eye and varying an amount of compression of actuation structure 120. Illustratively, a surgeon may aim optic fiber distal end 251 at any target within a particular sagittal plane of the inner eye by, e.g., rotating handle 100 to orient flexible housing tube 260 in an orientation configured to cause a curvature of flexible housing tube 260 within the particular sagittal plane of the inner eye and varying an amount of compression of actuation structure 120. In one or more embodiments, a surgeon may aim optic fiber distal end 251 at any target within a particular frontal plane of the inner eye by, e.g., varying an amount of compression of actuation structure 120 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 5A and 5B are schematic diagrams illustrating a handle 500. FIG. 5A illustrates a top view of handle 500. In one or more embodiments, handle 500 may comprise a handle distal end 501, a handle proximal end 502, a handle base 510, and an actuation structure 520. Illustratively, actuation structure 520 may comprise an actuation structure distal end 521 and an actuation structure proximal end 522. In one or more embodiments, actuation structure 520 may comprise a plurality of actuation arms 525. Illustratively, each actuation arm 525 may comprise at least one extension mechanism 526. In one or more embodiments, actuation structure 520 may comprise a shape memory material configured to project actuation structure distal end 521 a first distance from actuation structure proximal end 522, e.g., when actuation structure 520 is fully decompressed. Illustratively, actuation structure 520 may comprise a shape memory material configured to project actuation structure distal end 521 a second distance from actuation structure proximal end 522, e.g., when actuation structure 520 is fully compressed. In one or more embodiments, the second distance from actuation structure proximal end 522 may be greater than the first distance from actuation structure proximal end 522. Actuation structure 520 may be manufactured from any suitable material, e.g., polymers, metals, metal alloys, etc., or from any combination of suitable materials.

Illustratively, actuation structure 520 may be compressed by an application of a compressive force to actuation structure 520. In one or more embodiments, actuation structure 520 may be compressed by an application of one or more compressive forces located at one or more locations around an outer perimeter of actuation structure 520. Illustratively, the one or more locations may comprise any of a plurality of locations around the outer perimeter of actuation structure 520. For example, a surgeon may compress actuation structure 520 by squeezing actuation structure 520. Illustratively, the surgeon may compress actuation structure 520 by squeezing actuation structure 520 at any particular location of a plurality of locations around an outer perimeter of actuation structure 520. For example, a surgeon may rotate handle 500 and compress actuation structure 520 from any rotational position of a plurality of rotational positions of handle 500.

In one or more embodiments, actuation structure 520 may be compressed by an application of a compressive force to any one or more of the plurality of actuation arms 525. Illustratively, each actuation arm 525 may be configured to actuate independently. In one or more embodiments, each actuation arm 525 may be connected to one or more of the plurality of actuation arms 525 wherein an actuation of a particular actuation arm 525 may be configured to actuate every actuation arm 525 of the plurality of actuation arms 525. Illustratively, one or more actuation arms 525 may be configured to actuate in pairs or groups. For example, an actuation of a first actuation arm 525 may be configured to actuate a second actuation arm 525.

In one or more embodiments, a compression of actuation structure 520, e.g., due to an application of a compressive force to a particular actuation arm 525, may be configured to actuate the particular actuation arm 525. Illustratively, an actuation of the particular actuation arm 525 may be configured to actuate every actuation arm 525 of the plurality of actuation arms 525. In one or more embodiments, an application of a compressive force to a particular actuation arm 525 may be configured to extend at least one extension mechanism 526 of the particular actuation arm 525. Illustratively, a particular actuation arm 525 may be configured to extend a first length from handle base 510. An extension of an extension mechanism 526 of the particular actuation arm 525, e.g., due to an application of a compressive force to the particular actuation arm 525, may be configured to extend the particular actuation arm 525 a second length from handle base 510. Illustratively, the second length from handle base 510 may be greater than the first length from handle base 510.

In one or more embodiments, handle 500 may comprise an actuation ring 530 fixed to actuation structure distal end 521. Illustratively, a compression of actuation structure 520 may be configured to gradually extend actuation ring 530 from handle base 510. For example, actuation ring 530 may be configured to extend a first distance from actuation structure proximal end 522, e.g., when actuation structure 520 is fully decompressed. Actuation ring 530 may be configured to extend a second distance from actuation structure proximal end 522, e.g., due to a compression of actuation structure 520. Illustratively, the second distance from actuation structure proximal end 522 may be greater than the first distance from actuation structure proximal end 522.

FIG. 5B illustrates a cross-sectional view of handle 500. In one or more embodiments, handle 500 may comprise an inner bore 540, an inner bore proximal taper 550, a piston tube housing 560, and a fixation mechanism housing 570. Handle 500 may be manufactured from any suitable material, e.g., polymers, metals, metal alloys, etc., or from any combination of suitable materials.

Figure 6:
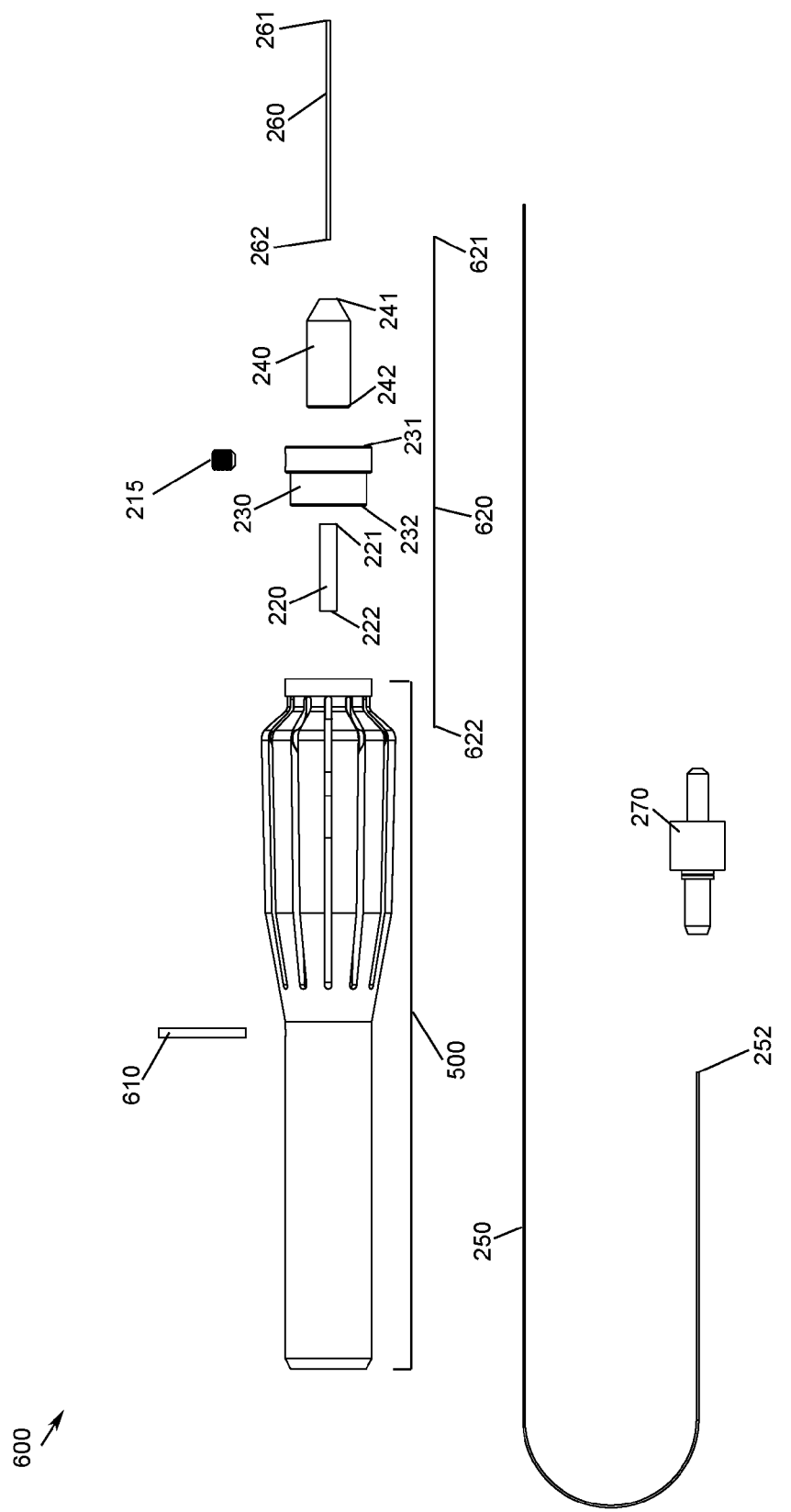
FIG. 6 is a schematic diagram illustrating an exploded view of a steerable laser probe assembly.

FIG. 6 is a schematic diagram illustrating an exploded view of a steerable laser probe assembly 600. In one or more embodiments, steerable laser probe assembly 600 may comprise a handle 500, a fixation mechanism 610, a nosecone fixation mechanism 215, a piston tube 220 having a piston tube distal end 221 and a piston tube proximal end 222, an outer nosecone 230 having an outer nosecone distal end 231 and an outer nosecone proximal end 232, an inner nosecone 240 having an inner nosecone distal end 241 and an inner nosecone proximal end 242, an optic fiber 250 having an optic fiber distal end 251 and an optic fiber proximal end 252, a wire 620 having a wire distal end 621 and a wire proximal end 622, a flexible housing tube 260 having a flexible housing tube distal end 261 and a flexible housing tube proximal end 262, and a light source interface 270. Illustratively, light source interface 270 may be configured to interface with optic fiber 250, e.g., at optic fiber proximal end 252. In one or more embodiments, light source interface 270 may comprise a standard light source connecter, e.g., an SMA connector.

In one or more embodiments, a portion of piston tube 220 may be disposed within piston tube housing 560, e.g., piston tube proximal end 222 may be disposed within piston tube housing 560. Illustratively, piston tube 220 may be fixed to outer nosecone 230, e.g., piston tube distal end 221 may be fixed to outer nosecone proximal end 232. In one or more embodiments, a portion of piston tube 220 may be disposed within a portion of outer nosecone 230, e.g., piston tube distal end 221 may be disposed within outer nosecone 230. Illustratively, a portion of piston tube 220 may be disposed within a portion of outer nosecone 230 wherein piston tube 220 is fixed to outer nosecone 230. In one or more embodiments, piston tube 220 may be fixed to outer nosecone 230, e.g., by an adhesive or any suitable fixation means. Illustratively, piston tube 220 and outer nosecone 230 may be manufactured as a single unit. Piston tube 220 and outer nosecone 230 may be manufactured from any suitable material, e.g., polymers, metals, metal alloys, etc., or from any combination of suitable materials.

Illustratively, inner nosecone 240 may be fixed to outer nosecone 230, e.g., inner nosecone proximal end 242 may be fixed to outer nosecone distal end 231. In one or more embodiments, a portion of inner nosecone 240 may be disposed within a portion of outer nosecone 230, e.g., inner nosecone proximal end 242 may be disposed within outer nosecone 230. Illustratively, a portion of inner nosecone 240 may be disposed within a portion of outer nosecone 230 wherein inner nosecone 240 is fixed to outer nosecone 230. In one or more embodiments, inner nosecone 240 may be fixed to outer nosecone 230, e.g., by an adhesive or any suitable fixation means. Illustratively, nosecone fixation mechanism 215 may be configured to fix inner nosecone 240 to outer nosecone 230. For example, nosecone fixation mechanism 215 may comprise a set screw configured to firmly attach inner nosecone 240 to outer nosecone 230. In one or more embodiments, inner nosecone 240 and outer nosecone 230 may be manufactured as a single unit Inner nosecone 240 and outer nosecone 230 may be manufactured from any suitable material, e.g., polymers, metals, metal alloys, etc., or from any combination of suitable materials.

Illustratively, outer nosecone 230 may be fixed to actuation structure 520, e.g., outer nosecone proximal end 232 may be fixed to handle distal end 501. In one or more embodiments, a portion of outer nosecone 230 may be disposed within actuation ring 530, e.g., outer nosecone proximal end 232 may be disposed within actuation ring 530. Illustratively, a portion of outer nosecone 230 may be disposed within actuation ring 530 wherein outer nosecone 230 is fixed to actuation ring 530. In one or more embodiments, outer nosecone 230 may be fixed to actuation structure 520, e.g., by an adhesive or any suitable fixation means.

Illustratively, a portion of flexible housing tube 260 may be fixed to inner nosecone 240, e.g., flexible housing tube proximal end 262 may be fixed to inner nosecone distal end 241. In one or more embodiments, a portion of flexible housing tube 260 may be fixed to inner nosecone 240, e.g., by an adhesive or any suitable fixation means. Illustratively, a portion of flexible housing tube 260 may be disposed within a portion of inner nosecone 240, e.g., flexible housing tube proximal end 262 may be disposed within a portion of inner nosecone 240. In one or more embodiments, a portion of flexible housing tube 260 may be fixed within inner nosecone 240, e.g., by an adhesive or any suitable fixation means. Flexible housing tube 260 may be manufactured from any suitable material, e.g., polymers, metals, metal alloys, etc., or from any combination of suitable materials. Illustratively, flexible housing tube 260 may comprise a shape memory material, e.g., Nitinol. In one or more embodiments, flexible housing tube 260 may be manufactured from a material having an ultimate tensile strength between 700 and 1000 MPa. Illustratively, flexible housing tube 260 may be manufactured from a material having ultimate tensile strength less than 700 MPa or greater than 1000 MPa. In one or more embodiments, flexible housing tube 260 may be manufactured from a material having a modulus of elasticity between 30 and 80 GPa. Illustratively, flexible housing tube 260 may be manufactured from a material having a modulus of elasticity less than 30 GPa or greater than 80 GPa.

In one or more embodiments, flexible housing tube 260 may be manufactured with dimensions suitable for performing microsurgical procedures, e.g., ophthalmic surgical procedures. Illustratively, flexible housing tube 260 may be manufactured at gauge sizes commonly used in ophthalmic surgical procedures, e.g., 23 gauge, 25 gauge, etc. In one or more embodiments, flexible housing tube 260 may be configured to be inserted in a cannula, e.g., a cannula used during an ophthalmic surgical procedure. For example, one or more properties of flexible housing tube 260 may be optimized to reduce friction as flexible housing tube 260 is inserted into a cannula. In one or more embodiments, one or more properties of flexible housing tube 260 may be optimized to reduce friction as flexible housing tube 260 is removed from a cannula. Illustratively, flexible housing tube 260 may have an ultimate tensile strength between 1000 MPa and 1100 MPa. In one or more embodiments, flexible housing tube 260 may have an ultimate tensile strength less than 1000 MPa or greater than 1100 MPa.

In one or more embodiments, optic fiber 250 may be disposed within inner bore 540, piston tube housing 560, piston tube 220, outer nosecone 230, inner nosecone 240, and flexible housing tube 260. Illustratively, optic fiber 250 may be disposed within flexible housing tube 260 wherein optic fiber distal end 251 is adjacent to flexible housing tube distal end 261. In one or more embodiments, a portion of optic fiber 250 may be fixed to a portion of flexible housing tube 260, e.g., by an adhesive or any suitable fixation means.

Illustratively, wire 620 may be disposed within fixation mechanism housing 570, inner bore 540, piston tube housing 560, piston tube 220, outer nosecone 230, inner nosecone 240, and flexible housing tube 260. In one or more embodiments, wire 620 may be disposed within flexible housing tube 260 wherein wire distal end 621 is adjacent to flexible housing tube distal end 261. Illustratively, a portion of wire 620 may be fixed to a portion of flexible housing tube 260, e.g., wire distal end 621 may be fixed to an inner portion of flexible housing tube 260. In one or more embodiments, a portion of wire 620 may be fixed to a portion of flexible housing tube 260, e.g., by an adhesive or any suitable fixation means. Illustratively, fixation mechanism 610 may be disposed within fixation mechanism housing 570. In one or more embodiments, fixation mechanism 610 may be configured to fix a portion of wire 620 in a position relative to handle base 510, e.g., fixation mechanism 610 may be configured to fix wire proximal end 622 in a position relative to handle base 510. Illustratively, fixation mechanism 610 may comprise a set screw configured to fix a portion of wire 620 in a position relative to handle base 510, e.g., by a press fit or any suitable fixation means. In one or more embodiments, a portion of wire 620 may be fixed to a portion of fixation mechanism 610, e.g., by an adhesive or any suitable fixation means. Illustratively, wire 620 may be fixed in a position relative to handle base 510 and fixed to a portion of flexible housing tube 260. Wire 620 may be manufactured from any suitable material, e.g., polymers, metals, metal alloys, etc., or from any combination of suitable materials.

In one or more embodiments, a compression of actuation structure 520 may be configured to extend actuation ring 530 relative to handle proximal end 502. Illustratively, an extension of actuation ring 530 relative to handle proximal end 502 may be configured to extend piston tube 220, outer nosecone 230, inner nosecone 240, and flexible housing tube 260 relative to handle proximal end 502. In one or more embodiments, an extension of flexible housing tube 260 relative to handle proximal end 502 may be configured to extend flexible housing tube 260 relative to wire 620. Illustratively, a compression of actuation structure 520 may be configured to extend flexible housing tube 260 relative to wire 620. In one or more embodiments, a portion of wire 620 may be configured to resist an extension of flexible housing tube 260, e.g., a portion of wire 620 that is fixed to flexible housing tube 260 may be configured to resist an extension of a portion of flexible housing tube 260 relative to handle proximal end 502. Illustratively, as flexible housing tube 260 is extended relative to wire 620, e.g., due to a compression of actuation structure 520, wire 620 may be configured to provide a resistive force, e.g., to resist an extension of a portion of flexible housing tube 260 relative to handle proximal end 502. In one or more embodiments, as flexible housing tube 260 is extended relative to handle proximal end 502, wire 620 may be configured to apply a compressive force to a portion of flexible housing tube 260. Illustratively, an application of a compressive or a resistive force to a portion of flexible housing tube 260 may be configured to compress a portion of flexible housing tube 260. In one or more embodiments, a compression of a portion of flexible housing tube 260 may be configured to cause flexible housing tube 260 to gradually curve. Illustratively, a gradual curving of flexible housing tube 260 may be configured to gradually curve optic fiber 250.

In one or more embodiments, a compression of actuation structure 520 may be configured to gradually curve optic fiber 250. Illustratively, a compression of actuation structure 520 may be configured to curve optic fiber 250 wherein a line tangent to optic fiber distal end 251 and a line tangent to optic fiber proximal end 252 may intersect at a curved optic fiber angle. In one or more embodiments, a compression of actuation structure 520 may be configured to curve flexible housing tube 260 wherein a line tangent to flexible housing tube distal end 261 may intersect a line tangent to flexible housing tube proximal end 262 at a curved flexible housing tube angle. Illustratively, a particular compression of actuation structure 520 may be configured to cause the curved optic fiber angle and the curved flexible housing tube angle to be equal, e.g., when wire 620 is fixed to flexible housing tube 260 at a single fixation point. In one or more embodiments, a particular compression of actuation structure 520 may be configured to cause the curved optic fiber angle to be no more than one degree less than the curved flexible housing tube angle, e.g., when wire 620 is fixed to flexible housing tube 260 at a single fixation point. Illustratively, a particular compression of actuation structure 520 may be configured to cause the curved optic fiber angle to be within a predetermined range of tolerance relative to the curved flexible housing tube angle. In one or more embodiments, a particular compression of actuation structure 520 may be configured to cause the curved optic fiber angle to be within five degrees of the curved flexible housing tube angle. Illustratively, optic fiber 250 may comprise a majority of the area inside flexible housing tube 260. In one or more embodiments, wire 620 may comprise a majority of the area inside flexible housing tube 260. Illustratively, wire 620 and optic fiber 250 may comprise a majority of the area inside flexible housing tube 260.

In one or more embodiments, a decompression of actuation structure 520 may be configured to retract actuation ring 530 relative to handle proximal end 502. Illustratively, a retraction of actuation ring 530 relative to handle proximal end 502 may be configured to retract piston tube 220, outer nosecone 230, inner nosecone 240, and flexible housing tube 260 relative to handle proximal end 502. In one or more embodiments, a refraction of flexible housing tube 260 relative to handle proximal end 502 may be configured to retract flexible housing tube 260 relative to wire 620. Illustratively, a decompression of actuation structure 520 may be configured to retract flexible housing tube 260 relative to wire 620. In one or more embodiments, a portion of wire 620 may be configured to facilitate a retraction of flexible housing tube 260, e.g., a portion of wire 620 that is fixed to flexible housing tube 260 may be configured to facilitate a retraction of a portion of flexible housing tube 260 relative to handle proximal end 502. Illustratively, as flexible housing tube 260 is retracted relative to wire 620, e.g., due to a decompression of actuation structure 520, wire 620 may be configured to reduce a resistive force, e.g., to facilitate a retraction of flexible housing tube 260 relative to handle proximal end 502. In one or more embodiments, as flexible housing tube 260 is retracted relative to handle proximal end 502, wire 620 may be configured to reduce a compressive force applied to a portion of flexible housing tube 260. Illustratively, a reduction of a compressive or a resistive force applied to a portion of flexible housing tube 260 may be configured to decompress a portion of flexible housing tube 260. In one or more embodiments, a decompression of a portion of flexible housing tube 260 may be configured to cause flexible housing tube 260 to gradually straighten. Illustratively, a gradual straightening of flexible housing tube 260 may be configured to gradually straighten optic fiber 250.

In one or more embodiments, a decompression of actuation structure 520 may be configured to gradually straighten optic fiber 250. Illustratively, a decompression of actuation structure 520 may be configured to straighten optic fiber 250 wherein a line tangent to optic fiber distal end 251 and a line tangent to optic fiber proximal end 252 may intersect at a straightened optic fiber angle. In one or more embodiments, a decompression of actuation structure 520 may be configured to straighten flexible housing tube 260 wherein a line tangent to flexible housing tube distal end 261 may intersect a line tangent to flexible housing tube proximal end 262 at a straightened flexible housing tube angle. Illustratively, a particular decompression of actuation structure 520 may be configured to cause the straightened optic fiber angle and the straightened flexible housing tube angle to be equal, e.g., when wire 620 is fixed to flexible housing tube 260 at a single fixation point. In one or more embodiments, a particular decompression of actuation structure 520 may be configured to cause the straightened optic fiber angle to be no more than one degree less than the straightened flexible housing tube angle, e.g., when wire 620 is fixed to flexible housing tube 260 at a single fixation point. Illustratively, a particular decompression of actuation structure 520 may be configured to cause the straightened optic fiber angle to be within a predetermined range of tolerance relative to the straightened flexible housing tube angle. In one or more embodiments, a particular decompression of actuation structure 520 may be configured to cause the straightened optic fiber angle to be within five degrees of the straightened flexible housing tube angle.

Figure 7A:
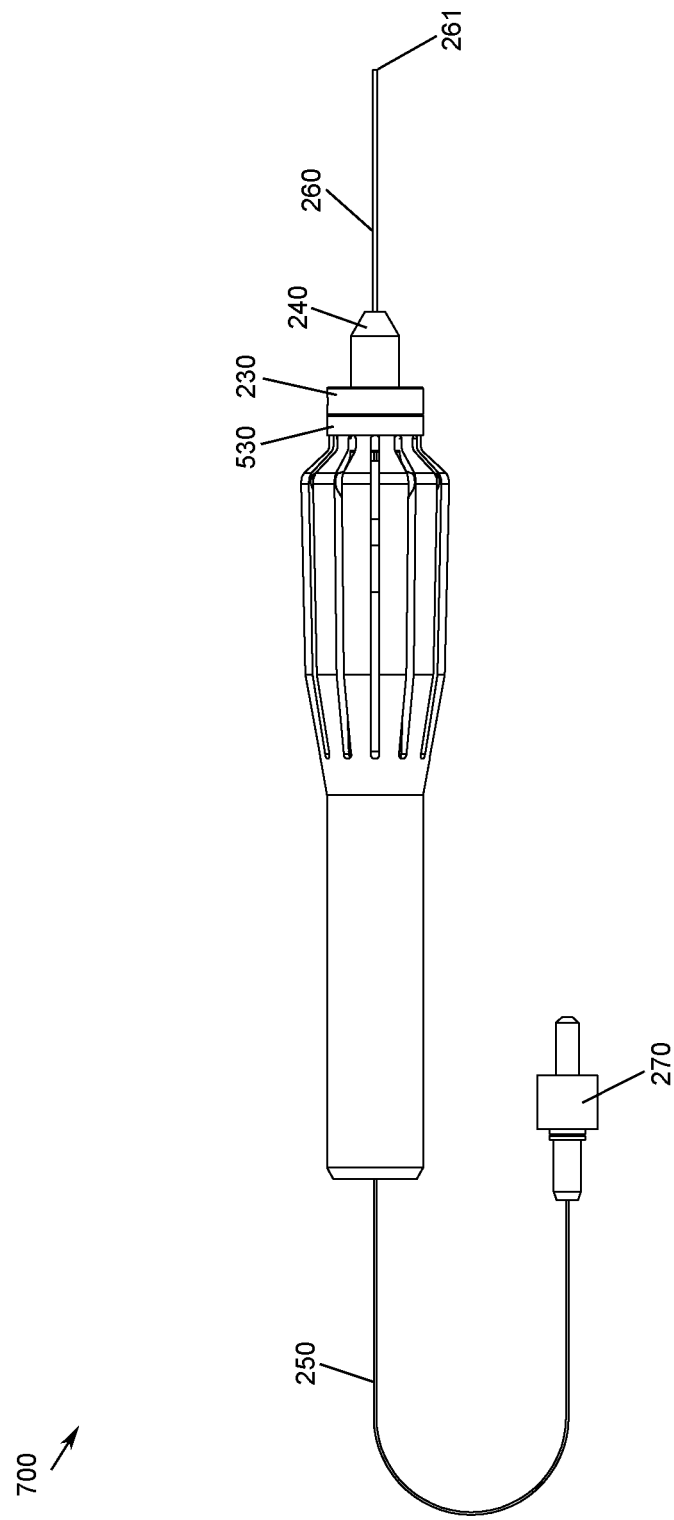
FIGS. 7A, 7B, 7C, 7D, and 7E illustrate a gradual curving of an optic fiber.

FIGS. 7A, 7B, 7C, 7D, and 7E illustrate a gradual curving of an optic fiber 250. FIG. 7A illustrates a straight optic fiber 700. In one or more embodiments, optic fiber 250 may comprise a straight optic fiber 700, e.g., when flexible housing tube 260 is fully refracted relative to handle proximal end 502. Illustratively, optic fiber 250 may comprise a straight optic fiber 700, e.g., when actuation structure 520 is fully decompressed. In one or more embodiments, optic fiber 250 may comprise a straight optic fiber 700, e.g., when actuation ring 530 is fully refracted relative to handle proximal end 502. Illustratively, a line tangent to optic fiber distal end 251 may be parallel to a line tangent to flexible housing tube proximal end 262, e.g., when optic fiber 250 comprises a straight optic fiber 700.

Figure 7B:
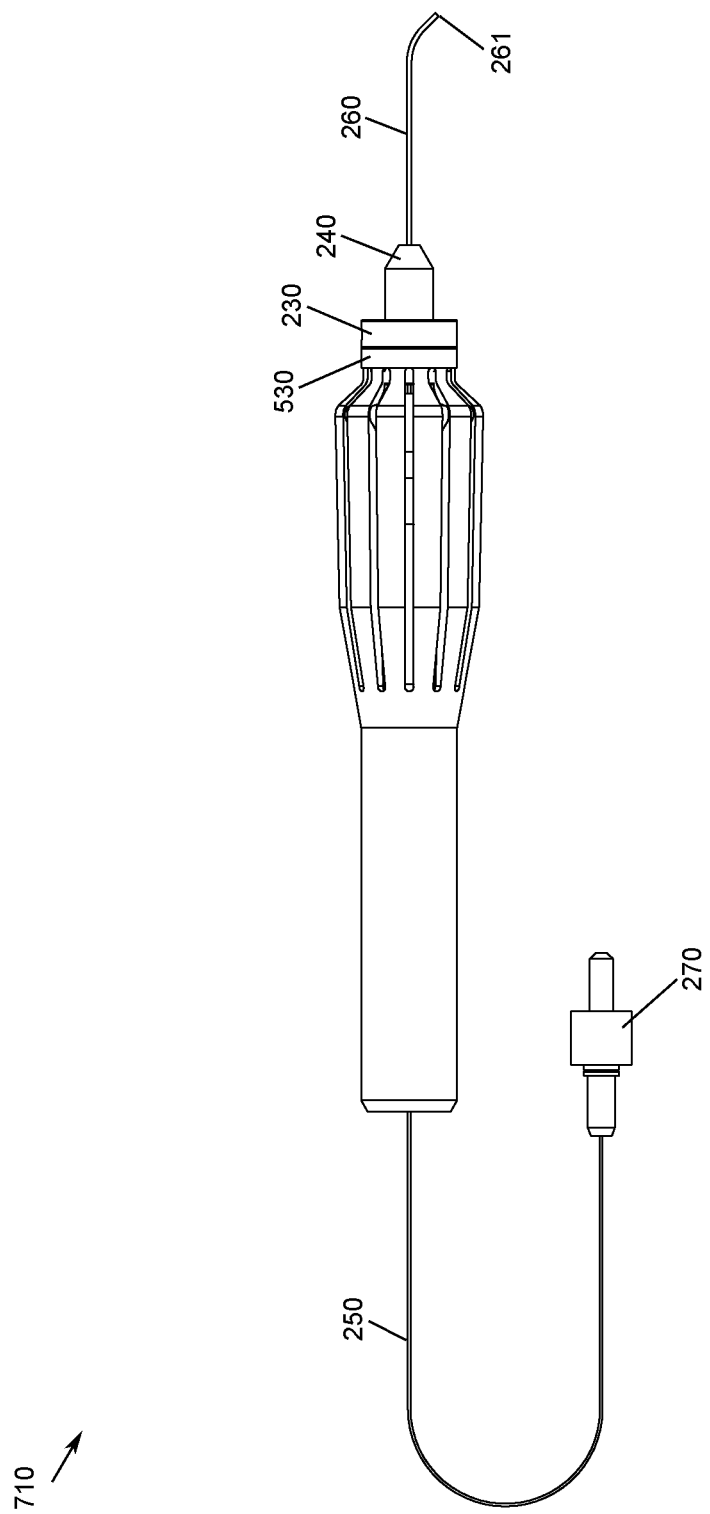

FIG. 7B illustrates an optic fiber in a first curved position 710. In one or more embodiments, a compression of actuation structure 520 may be configured to gradually curve optic fiber 250 from a straight optic fiber 700 to an optic fiber in a first curved position 710. Illustratively, a compression of actuation structure 520 may be configured to extend actuation ring 530 relative to handle proximal end 502. In one or more embodiments, an extension of actuation ring 530 relative to handle proximal end 502 may be configured to extend flexible housing tube 260 relative to wire 620. Illustratively, an extension of flexible housing tube 260 relative to wire 620 may be configured to apply a force to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to resist an extension of flexible housing tube 260 relative to wire 620. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from a straight optic fiber 700 to an optic fiber in a first curved position 710. Illustratively, a line tangent to optic fiber distal end 251 may intersect a line tangent to flexible housing tube proximal end 262 at a first angle, e.g., when optic fiber 250 comprises an optic fiber in a first curved position 710. In one or more embodiments, the first angle may comprise any angle greater than zero degrees. For example, the first angle may comprise a 45 degree angle.

Figure 7C:
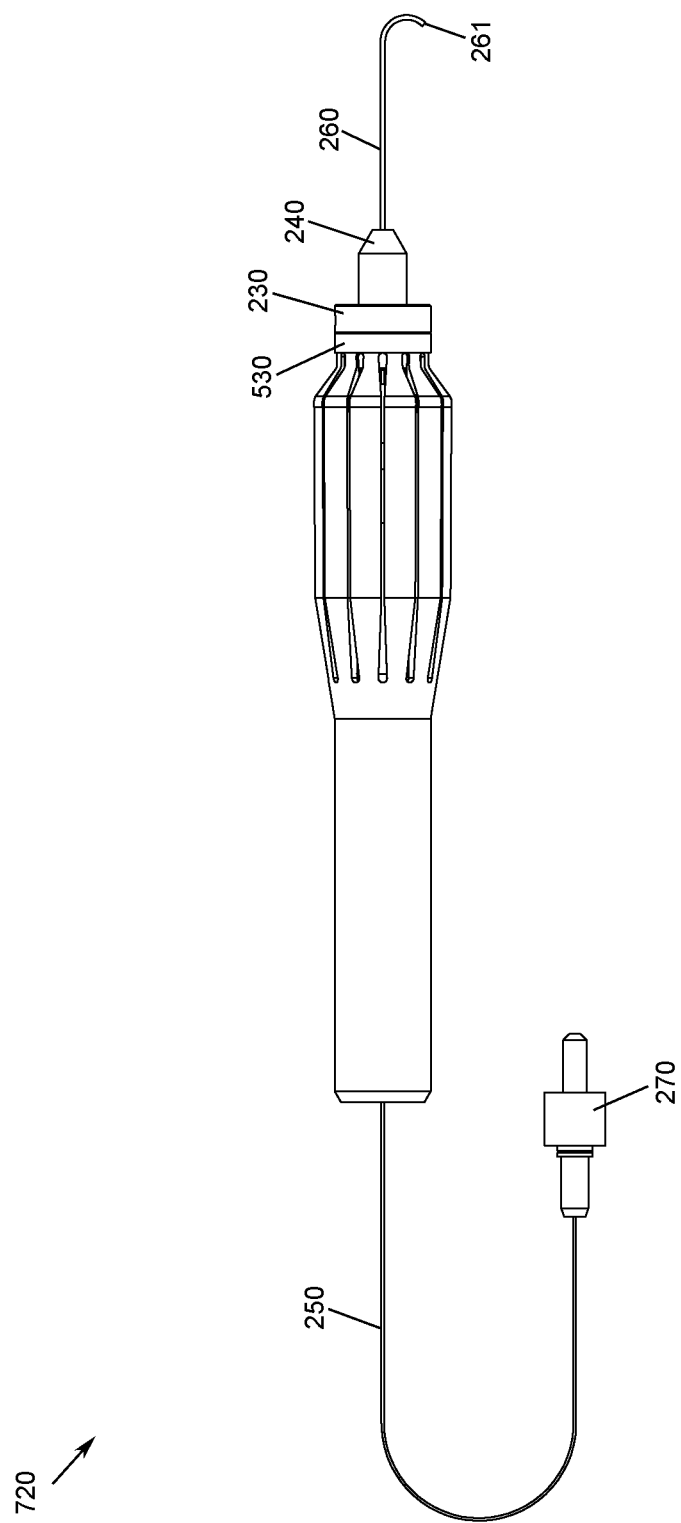

FIG. 7C illustrates an optic fiber in a second curved position 720. In one or more embodiments, a compression of actuation structure 520 may be configured to gradually curve optic fiber 250 from an optic fiber in a first curved position 710 to an optic fiber in a second curved position 720. Illustratively, a compression of actuation structure 520 may be configured to extend actuation ring 530 relative to handle proximal end 502. In one or more embodiments, an extension of actuation ring 530 relative to handle proximal end 502 may be configured to extend flexible housing tube 260 relative to wire 620. Illustratively, an extension of flexible housing tube 260 relative to wire 620 may be configured to apply a force to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to resist an extension of flexible housing tube 260 relative to wire 620. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from an optic fiber in a first curved position 710 to an optic fiber in a second curved position 720. Illustratively, a line tangent to optic fiber distal end 251 may intersect a line tangent to flexible housing tube proximal end 262 at a second angle, e.g., when optic fiber 250 comprises an optic fiber in a second curved position 720. In one or more embodiments, the second angle may comprise any angle greater than the first angle. For example, the second angle may comprise a 90 degree angle.

Figure 7D:
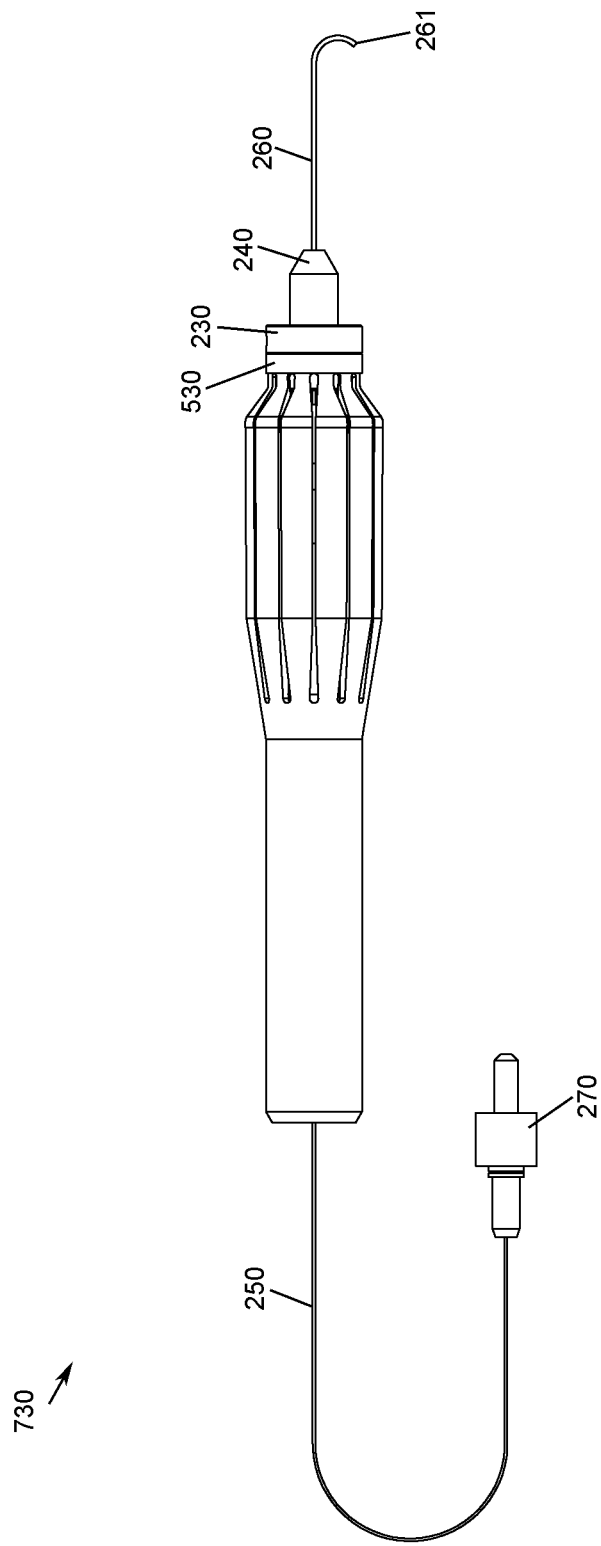

FIG. 7D illustrates an optic fiber in a third curved position 730. In one or more embodiments, a compression of actuation structure 520 may be configured to gradually curve optic fiber 250 from an optic fiber in a second curved position 720 to an optic fiber in a third curved position 730. Illustratively, a compression of actuation structure 520 may be configured to extend actuation ring 530 relative to handle proximal end 502. In one or more embodiments, an extension of actuation ring 530 relative to handle proximal end 502 may be configured to extend flexible housing tube 260 relative to wire 620. Illustratively, an extension of flexible housing tube 260 relative to wire 620 may be configured to apply a force to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to resist an extension of flexible housing tube 260 relative to wire 620. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from an optic fiber in a second curved position 720 to an optic fiber in a third curved position 730. Illustratively, a line tangent to optic fiber distal end 251 may intersect a line tangent to flexible housing tube proximal end 262 at a third angle, e.g., when optic fiber 250 comprises an optic fiber in a third curved position 730. In one or more embodiments, the third angle may comprise any angle greater than the second angle. For example, the third angle may comprise a 135 degree angle.

Figure 7E:
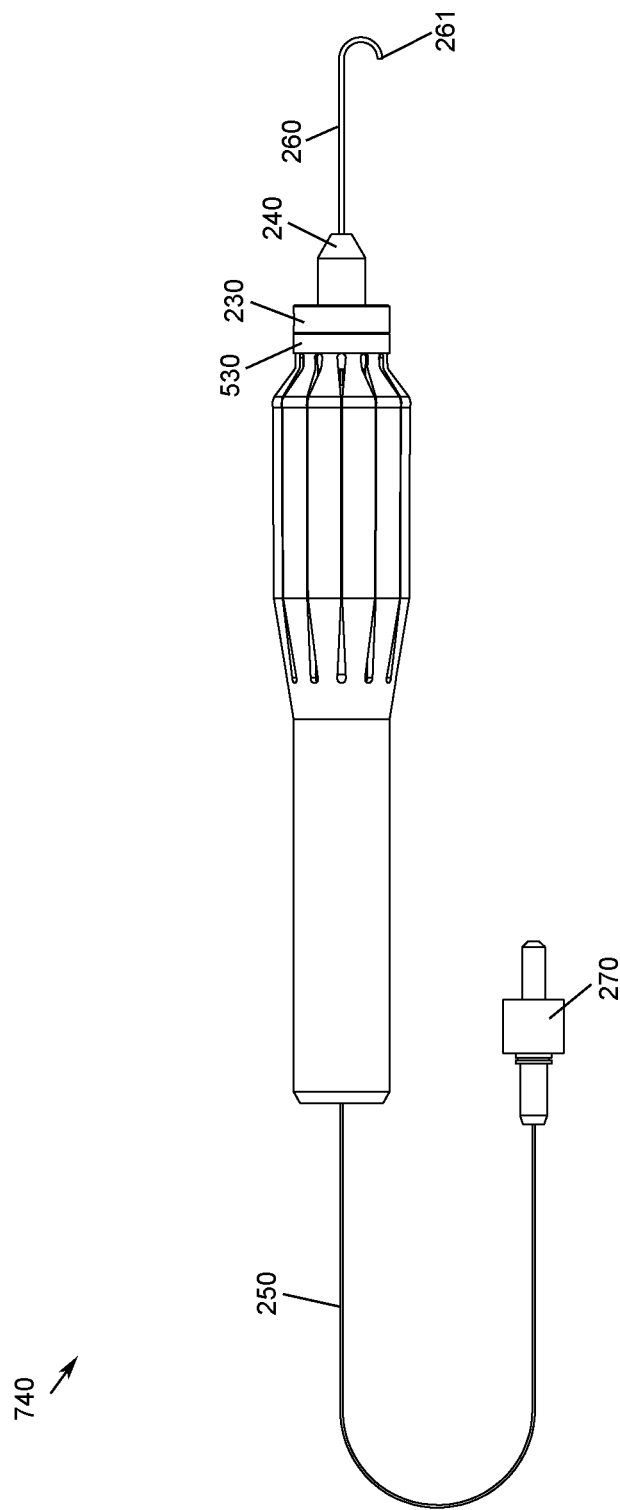

FIG. 7E illustrates an optic fiber in a fourth curved position 740. In one or more embodiments, a compression of actuation structure 520 may be configured to gradually curve optic fiber 250 from an optic fiber in a third curved position 730 to an optic fiber in a fourth curved position 740. Illustratively, a compression of actuation structure 520 may be configured to extend actuation ring 530 relative to handle proximal end 502. In one or more embodiments, an extension of actuation ring 530 relative to handle proximal end 502 may be configured to extend flexible housing tube 260 relative to wire 620. Illustratively, an extension of flexible housing tube 260 relative to wire 620 may be configured to apply a force to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to resist an extension of flexible housing tube 260 relative to wire 620. Illustratively, an application of a force to a portion of flexible housing tube 260 may be configured to compress a portion of flexible housing tube 260 causing flexible housing tube 260 to gradually curve. In one or more embodiments, a gradual curving of flexible housing tube 260 may be configured to gradually curve optic fiber 250, e.g., from an optic fiber in a third curved position 730 to an optic fiber in a fourth curved position 740. Illustratively, a line tangent to optic fiber distal end 251 may be parallel to a line tangent to flexible housing tube proximal end 262, e.g., when optic fiber 250 comprises an optic fiber in a fourth curved position 740.

In one or more embodiments, one or more properties of a steerable laser probe may be adjusted to attain one or more desired steerable laser probe features. For example, a length that flexible housing tube distal end 261 extends from inner nosecone distal end 241 may be adjusted to vary an amount of compression of actuation structure 520 configured to curve flexible housing tube 260 to a particular curved position. In one or more embodiments, a stiffness of flexible housing tube 260 may be adjusted to vary an amount of compression of actuation structure 520 configured to curve flexible housing tube 260 to a particular curved position. Illustratively, a material comprising flexible housing tube 260 may be adjusted to vary an amount of compression of actuation structure 520 configured to curve flexible housing tube 260 to a particular curved position. In one or more embodiments, a stiffness of flexible housing tube 260 may be adjusted to vary a bend radius of flexible housing tube 260. For example, a stiffness of flexible housing tube 260 may be adjusted to vary a radius of curvature of flexible housing tube 260, e.g., when flexible housing tube 260 is in a particular curved position.

Illustratively, a distance that inner nosecone distal end 241 extends from outer nosecone distal end 231 may be adjusted, e.g., to vary an amount of compression of actuation structure 520 configured to curve flexible housing tube 260 to a particular curved position. For example, an amount of compression of actuation structure 520 configured to curve flexible housing tube 260 to a particular curved position may be reduced, e.g., by increasing a distance that inner nosecone distal end 241 extends from outer nosecone distal end 231. In one or more embodiments, an amount of compression of actuation structure 520 configured to curve flexible housing tube 260 to a particular curved position may be increased, e.g., by decreasing a distance that inner nosecone distal end 241 extends from outer nosecone distal end 231. Illustratively, a steerable laser probe may comprise a mechanism configured to adjust a distance that inner nosecone distal end 241 extends from outer nosecone distal end 231, e.g., a surgeon or a surgeon's assistant may adjust a relative orientation of inner nosecone 240 and outer nosecone 230 before a surgical procedure. For example, a mechanism may be configured to expand or collapse a portion of nosecone fixation mechanism 215. In one or more embodiments, an expansion of a portion of nosecone fixation mechanism 215 may be configured to increase a distance that inner nosecone distal end 241 extends from outer nosecone distal end 231. Illustratively, a collapse of a portion of nosecone fixation mechanism 215 may be configured to decrease a distance that inner nosecone distal end 241 extends from outer nosecone distal end 231.

In one or more embodiments, a geometry of actuation structure 520 may be adjusted to vary an amount of compression of actuation structure 520 configured to curve flexible housing tube 260 to a particular curved position. Illustratively, one or more locations within flexible housing tube 260 wherein wire 620 may be fixed to an inner portion of flexible housing tube 260 may be adjusted to vary an amount of compression of actuation structure 520 configured to curve flexible housing tube 260 to a particular curved position. In one or more embodiments, wire 620 may be fixed to flexible housing tube 260 at a plurality of fixation points, e.g., to vary one or more properties of a steerable laser probe. Illustratively, a length of wire 620 may be adjusted to vary an amount of compression of actuation structure 520 configured to curve flexible housing tube 260 to a particular curved position. In one or more embodiments, at least a portion of optic fiber 250 may be enclosed in an optic fiber sleeve configured to, e.g., protect optic fiber 250, vary a stiffness of optic fiber 250, vary an optical property of optic fiber 250, etc. Illustratively, a steerable laser probe may comprise one or more redundant wires 620. In one or more embodiments, one or more redundant wires 620 may be configured to maintain a particular curved position of flexible housing tube 260, e.g., in the event that wire 620 breaks. Illustratively, one or more redundant wires 620 may be configured to maintain a particular curved position of flexible housing tube 260, e.g., in the event that a wire 620 fixation means fails. In one or more embodiments, one or more redundant wires 620 may be configured to maintain a particular curved position of flexible housing tube 260, e.g., in the event that wire 620 is no longer configured to maintain the particular curved position of flexible housing tube 620. Illustratively, one or more redundant wires 620 may be configured to maintain a particular curved position of flexible housing tube 260 wherein wire 620 is also configured to maintain the particular curved position of flexible housing tube 260.

Illustratively, a steerable laser probe may be configured to indicate, e.g., to a surgeon, a direction that optic fiber 250 may curve, e.g., due to a compression of actuation structure 520. In one or more embodiments, a portion of a steerable laser probe, e.g., handle 500, may be marked in a manner configured to indicate a direction that optic fiber 250 may curve. For example, a portion of flexible housing tube 260 may comprise a mark configured to indicate a direction that optic fiber 250 may curve. Illustratively, flexible housing tube 260 may comprise a slight curve, e.g., a curve less than 7.5 degrees, when actuation structure 520 is fully decompressed. In one or more embodiments, flexible housing tube 260 may comprise a slight curve configured to indicate a direction that optic fiber 250 may curve, e.g., due to a compression of actuation structure 520. Illustratively, a steerable laser probe may comprise a mechanism configured to allow a surgeon or a surgeon's assistant to adjust a degree of a slight curve in flexible housing tube 260. For example, a steerable laser probe may comprise a mechanism configured to expand or collapse nosecone fixation mechanism 215.

Figure 8A:
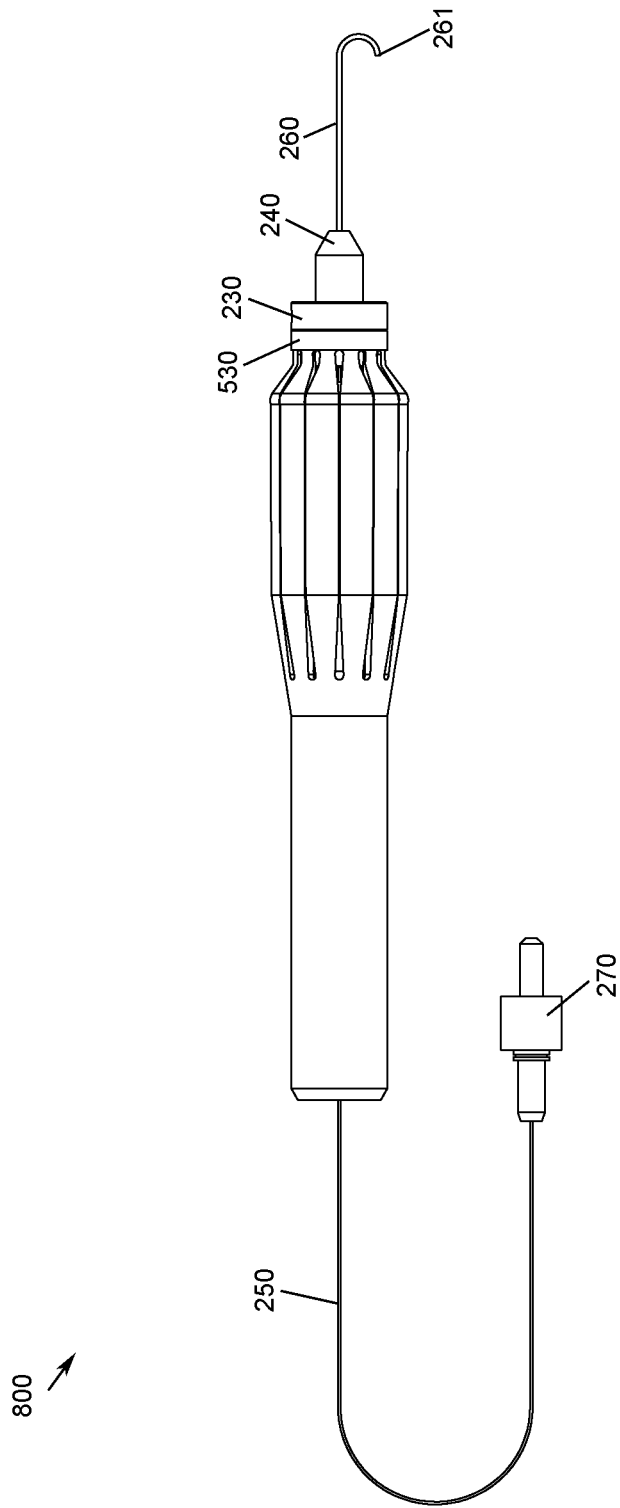
FIGS. 8A, 8B, 8C, 8D, and 8E illustrate a gradual straightening of an optic fiber.

FIGS. 8A, 8B, 8C, 8D, and 8E illustrate a gradual straightening of an optic fiber 250. FIG. 8A illustrates a fully curved optic fiber 800. In one or more embodiments, optic fiber 250 may comprise a fully curved optic fiber 800, e.g., when flexible housing tube 260 is fully extended relative to wire 620. For example, optic fiber 250 may comprise a fully curved optic fiber 800 when actuation ring 530 is fully extended relative to handle proximal end 502. Illustratively, optic fiber 250 may comprise a fully curved optic fiber 800, e.g., when a portion of flexible housing tube 260 is compressed. In one or more embodiments, optic fiber 250 may comprise a fully curved optic fiber 800, e.g., when actuation structure 520 is fully compressed. Illustratively, a line tangent to optic fiber distal end 251 may be parallel to a line tangent to flexible housing tube proximal end 262, e.g., when optic fiber 250 comprises a fully curved optic fiber 800.

Figure 8B:
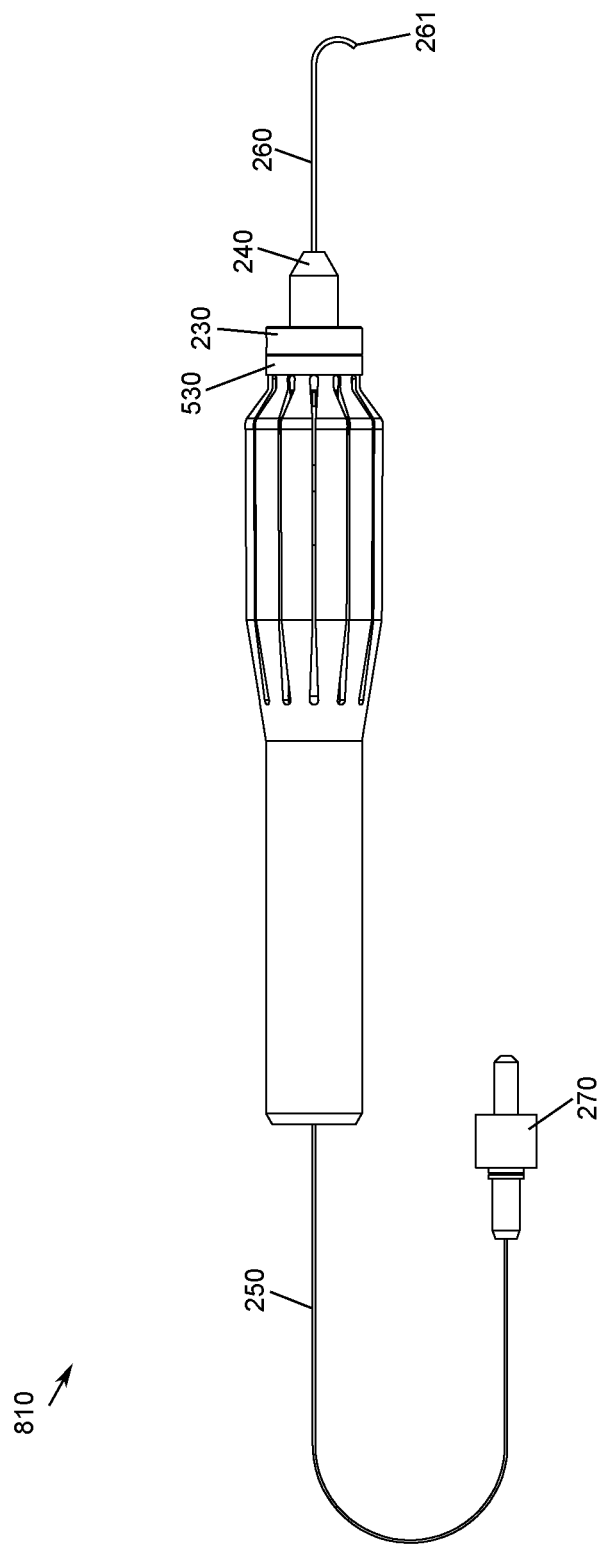

FIG. 8B illustrates an optic fiber in a first partially straightened position 810. In one or more embodiments, a decompression of actuation structure 520 may be configured to gradually straighten optic fiber 250 from a fully curved optic fiber 800 to an optic fiber in a first partially straightened position 810. Illustratively, a decompression of actuation structure 520 may be configured to retract actuation ring 530 relative to handle proximal end 502. In one or more embodiments, a retraction of actuation ring 530 relative to handle proximal end 502 may be configured to retract flexible housing tube 260 relative to wire 620. Illustratively, a retraction of flexible housing tube 260 relative to wire 620 may be configured to reduce a force applied to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to facilitate a retraction of flexible housing tube 260 relative to wire 620. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from a fully curved optic fiber 800 to an optic fiber in a first partially straightened position 810. Illustratively, a line tangent to optic fiber distal end 251 may intersect a line tangent to flexible housing tube proximal end 262 at a first partially straightened angle, e.g., when optic fiber 250 comprises an optic fiber in a first partially straightened position 810. In one or more embodiments, the first partially straightened angle may comprise any angle less than 180 degrees. For example, the first partially straightened angle may comprise a 135 degree angle.

Figure 8C:
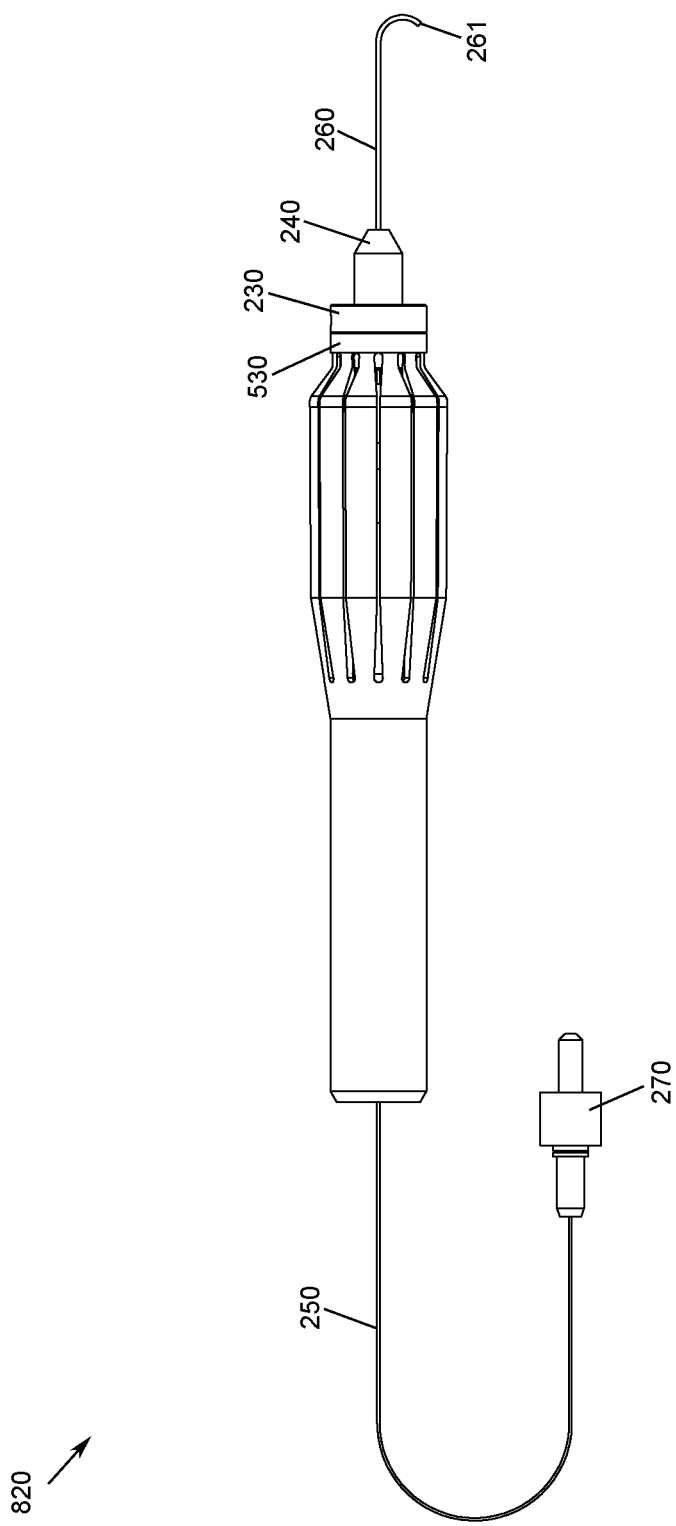

FIG. 8C illustrates an optic fiber in a second partially straightened position 820. In one or more embodiments, a decompression of actuation structure 520 may be configured to gradually straighten optic fiber 250 from an optic fiber in a first partially straightened position 810 to an optic fiber in a second partially straightened position 820. Illustratively, a decompression of actuation structure 520 may be configured to retract actuation ring 530 relative to handle proximal end 502. In one or more embodiments, a retraction of actuation ring 530 relative to handle proximal end 502 may be configured to retract flexible housing tube 260 relative to wire 620. Illustratively, a retraction of flexible housing tube 260 relative to wire 620 may be configured to reduce a force applied to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to facilitate a retraction of flexible housing tube 260 relative to wire 620. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from an optic fiber in a first partially straightened position 810 to an optic fiber in a second partially straightened position 820. Illustratively, a line tangent to optic fiber distal end 251 may intersect a line tangent to flexible housing tube proximal end 262 at a second partially straightened angle, e.g., when optic fiber 250 comprises an optic fiber in a second partially straightened position 820. In one or more embodiments, the second partially straightened angle may comprise any angle less than the first partially straightened angle. For example, the second partially straightened angle may comprise a 90 degree angle.

Figure 8D:
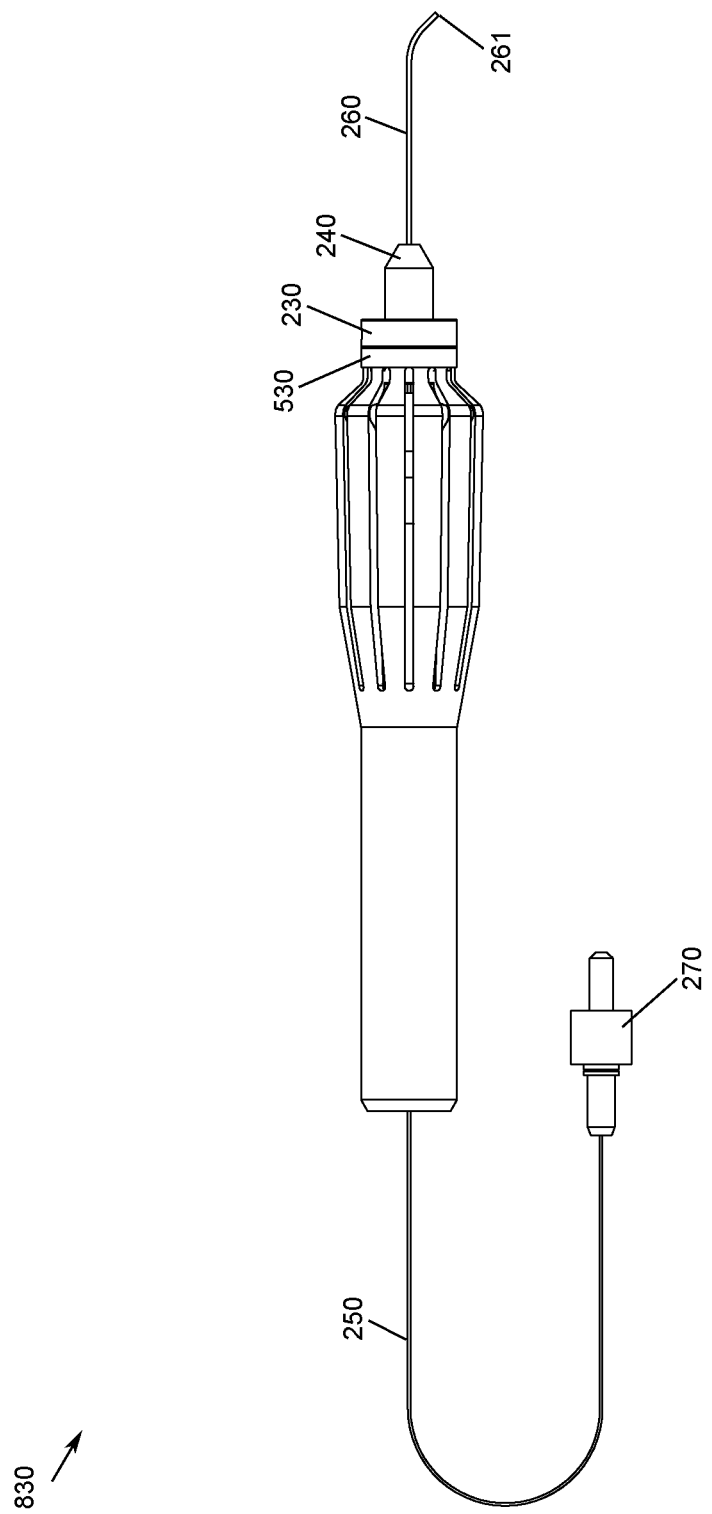

FIG. 8D illustrates an optic fiber in a third partially straightened position 830. In one or more embodiments, a decompression of actuation structure 520 may be configured to gradually straighten optic fiber 250 from an optic fiber in a second partially straightened position 820 to an optic fiber in a third partially straightened position 830. Illustratively, a decompression of actuation structure 520 may be configured to retract actuation ring 530 relative to handle proximal end 502. In one or more embodiments, a retraction of actuation ring 530 relative to handle proximal end 502 may be configured to retract flexible housing tube 260 relative to wire 620. Illustratively, a retraction of flexible houses ing tube 260 relative to wire 620 may be configured to reduce a force applied to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to facilitate a retraction of flexible housing tube 260 relative to wire 620. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from an optic fiber in a second partially straightened position 820 to an optic fiber in a third partially straightened position 830. Illustratively, a line tangent to optic fiber distal end 251 may intersect a line tangent to flexible housing tube proximal end 262 at a third partially straightened angle, e.g., when optic fiber 250 comprises an optic fiber in a third partially straightened position 830. In one or more embodiments, the third partially straightened angle may comprise any angle less than the second partially straightened angle. For example, the third partially straightened angle may comprise a 45 degree angle.

Figure 8E:
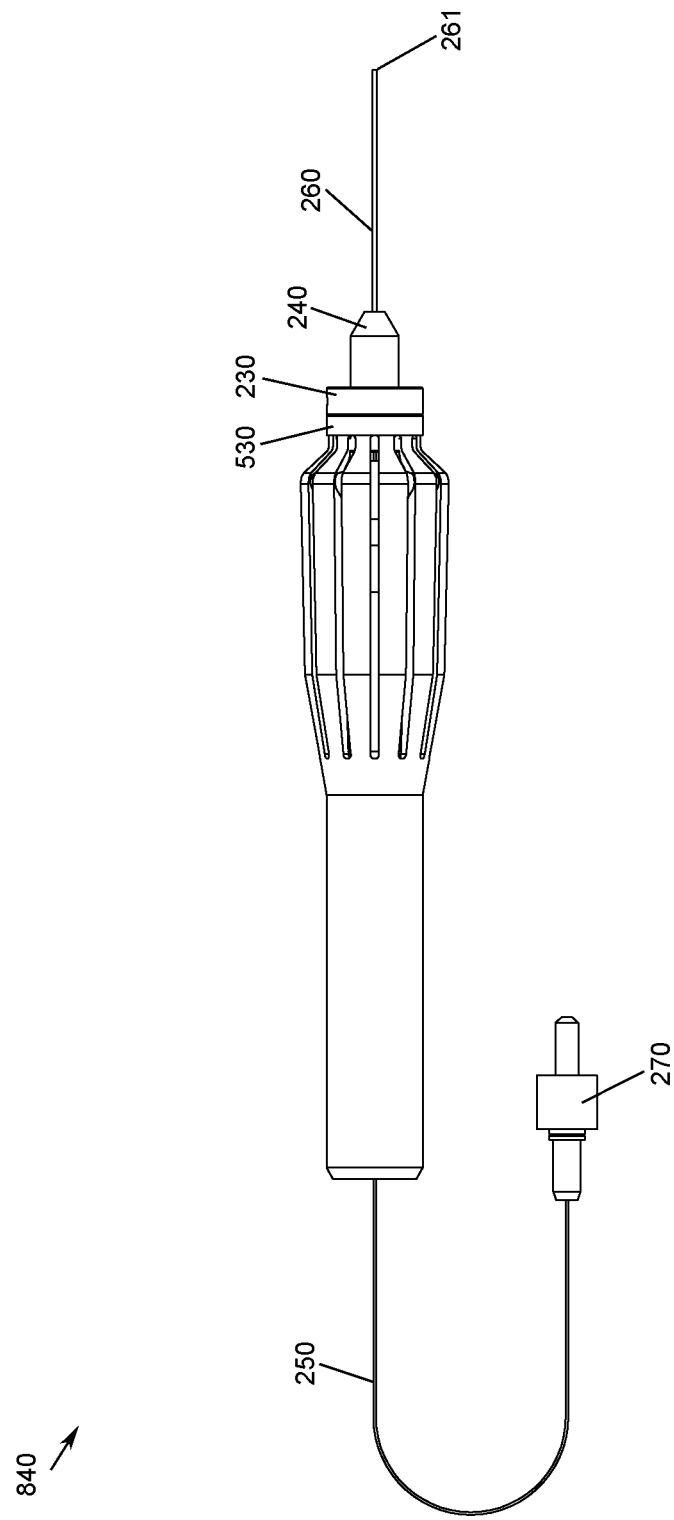

FIG. 8E illustrates an optic fiber in a fully straightened position 840. In one or more embodiments, a decompression of actuation structure 520 may be configured to gradually straighten optic fiber 250 from an optic fiber in a third partially straightened position 830 to an optic fiber in a fully straightened position 840. Illustratively, a decompression of actuation structure 520 may be configured to retract actuation ring 530 relative to handle proximal end 502. In one or more embodiments, a retraction of actuation ring 530 relative to handle proximal end 502 may be configured to retract flexible housing tube 260 relative to wire 620. Illustratively, a retraction of flexible housing tube 260 relative to wire 620 may be configured to reduce a force applied to a portion of flexible housing tube 260. In one or more embodiments, wire 620 may be fixed in a position relative to handle base 510 and wire 620 may also be fixed to a portion of flexible housing tube 260. For example, a portion of wire 620 may be configured to facilitate a retraction of flexible housing tube 260 relative to wire 620. Illustratively, a reduction of a force applied to a portion of flexible housing tube 260 may be configured to decompress a portion of flexible housing tube 260 causing flexible housing tube 260 to gradually straighten. In one or more embodiments, a gradual straightening of flexible housing tube 260 may be configured to gradually straighten optic fiber 250, e.g., from an optic fiber in a third partially straightened position 830 to an optic fiber in a fully straightened position 840. Illustratively, a line tangent to optic fiber distal end 251 may be parallel to a line tangent to flexible housing tube proximal end 262, e.g., when optic fiber 250 comprises an optic fiber in a fully straightened position 840.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 500 to orient flexible housing tube 260 in an orientation configured to cause a curvature of flexible housing tube 260 within the particular transverse plane of the inner eye and varying an amount of compression of actuation structure 520. Illustratively, a surgeon may aim optic fiber distal end 251 at any target within a particular sagittal plane of the inner eye by, e.g., rotating handle 500 to orient flexible housing tube 260 in an orientation configured to cause a curvature of flexible housing tube 260 within the particular sagittal plane of the inner eye and varying an amount of compression of actuation structure 520. In one or more embodiments, a surgeon may aim optic fiber distal end 251 at any target within a particular frontal plane of the inner eye by, e.g., varying an amount of compression of actuation structure 520 to orient a line tangent to optic fiber distal end 251 wherein the line tangent to optic fiber distal end 251 is within the particular frontal plane of the inner eye and rotating handle 500. Illustratively, a surgeon may aim optic fiber distal end 251 at any target located outside of the particular transverse plane, the particular sagittal plane, and the particular frontal plane of the inner eye, e.g., by varying a rotational orientation of handle 500 and varying an amount of compression of actuation structure 520. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:
1. An instrument comprising:
a handle having a handle distal end and a handle proximal end;
an actuation structure of the handle, the actuation structure having an actuation ring;
a plurality of actuation arms of the actuation structure, each actuation arm of the plurality of actuation arms having at least one extension mechanism;
an outer nosecone having an outer nosecone distal end and an outer nosecone proximal end, the outer nosecone proximal end disposed within the actuation ring;
a piston tube having a piston tube distal end and a piston tube proximal end, the piston tube distal end disposed within the outer nosecone;
an inner nosecone having an inner nosecone distal end and an inner nosecone proximal end, the inner nosecone disposed within the outer nosecone wherein the inner nosecone distal end extends a distance from the outer nosecone distal end;
an inner bore of the handle;
a piston tube housing of the handle, the piston tube proximal end disposed within the piston tube housing of the handle;
a single flexible housing tube having a flexible housing tube distal end and a flexible housing tube proximal end, the flexible housing tube having dimensions configured for performing ophthalmic microsurgical procedures through a cannula; and
an optic fiber disposed in the inner bore of the handle, the flexible housing tube, the piston tube, the outer nosecone, and the inner nosecone.

2. The instrument of claim 1 wherein a compression of the actuation structure is configured to gradually curve the optic fiber within an eye.

3. The instrument of claim 2 wherein the compression of the actuation structure is configured to gradually curve the optic fiber at least 45 degrees within the eye.

4. The instrument of claim 3 wherein the compression of the actuation structure is configured to gradually curve the optic fiber at least 45 degrees within the eye without increasing a length of the instrument in the eye.

5. The instrument of claim 3 wherein the compression of the actuation structure is configured to gradually curve the optic fiber at least 45 degrees within the eye without decreasing a length of the instrument in the eye.

6. The instrument of claim 1 further comprising:
a mark of the handle configured to indicate a direction of curvature of the optic fiber in response to a compression of the actuation structure.

7. The instrument of claim 1 further comprising:
a wire having a wire distal end and a wire proximal end, the wire disposed within the inner bore of the handle and the flexible housing tube wherein the wire proximal end is fixed to a portion of the handle and the wire distal end is fixed within the flexible housing tube.

8. The instrument of claim 7 further comprising:
a redundant wire having a redundant wire distal end and a redundant wire proximal end, the redundant wire disposed within the inner bore of the handle and the flexible housing tube wherein the redundant wire proximal end is fixed to the portion of the handle and the redundant wire distal end is fixed within the flexible housing tube.

9. The instrument of claim 8 wherein the redundant wire is configured to maintain a particular curved position of the flexible housing tube when the wire is not configured to maintain the particular curved position of the flexible housing tube.

10. An instrument comprising:
a handle having a handle distal end and a handle proximal end;
an actuation structure of the handle, the actuation structure having an actuation ring;
a plurality of actuation arms of the actuation structure, each actuation arm of the plurality of actuation arms having at least one extension mechanism;
an outer nosecone having an outer nosecone distal end and an outer nosecone proximal end, the outer nosecone proximal end disposed within the actuation ring;
an inner nosecone having an inner nosecone distal end and an inner nosecone proximal end, the inner nosecone disposed within the outer nosecone wherein the inner nosecone distal end extends a distance from the outer nosecone distal end;
a nosecone fixation mechanism configured to adjust the distance that the inner nosecone distal end extends from the outer nosecone distal end;
an inner bore of the handle;
a single flexible housing tube having a flexible housing tube distal end and a flexible housing tube proximal end, the flexible housing tube having dimensions configured for performing ophthalmic microsurgical procedures through a cannula;
an optic fiber disposed in the inner bore of the handle, the flexible housing tube, and the nosecone;
a wire having a wire distal end and a wire proximal end, the wire disposed within the inner bore of the handle and the flexible housing tube wherein the wire proximal end is fixed to a portion of the handle and the wire distal end is fixed within the flexible housing tube; and
a redundant wire having a redundant wire distal end and a redundant wire proximal end, the redundant wire disposed within the inner bore of the handle and the flexible housing tube wherein the redundant wire proximal end is fixed to the portion of the handle and the redundant wire distal end is fixed within the flexible housing tube and wherein the redundant wire is configured to maintain a particular curved position of the flexible housing tube when the wire is not configured to maintain the particular curved position of the flexible housing tube.

11. The instrument of claim 10 wherein a compression of the actuation structure is configured to gradually curve the optic fiber within an eye.

12. The instrument of claim 11 wherein the compression of the actuation structure is configured to gradually curve the optic fiber at least 45 degrees within the eye.

13. The instrument of claim 12 wherein the compression of the actuation structure is configured to gradually curve the optic fiber at least 45 degrees within the eye without increasing a length of the instrument in the eye.

14. The instrument of claim 12 wherein the compression of the actuation structure is configured to gradually curve the optic fiber at least 45 degrees within the eye without decreasing a length of the instrument in the eye.

15. The instrument of claim 10 further comprising:
a mark of the handle configured to indicate a direction of curvature of the optic fiber in response to a compression of the actuation structure.

16. The instrument of claim 10 wherein a decompression of the actuation structure is configured to gradually straighten the optic fiber within an eye.

17. The instrument of claim 16 wherein the decompression of the actuation structure is configured to gradually straighten the optic fiber within the eye without increasing a length of the instrument in the eye.

18. The instrument of claim 17 wherein the decompression of the actuation structure is configured to gradually straighten the optic fiber within the eye without decreasing a length of the instrument in the eye.

19. The instrument of claim 10 wherein the optic fiber comprises a majority of an area inside of the flexible housing tube.

20. The instrument of claim 10 wherein the optic fiber and the wire comprises a majority of an area inside of the flexible housing tube.

* * * * *